(12) United States Patent
Jiang et al.

(10) Patent No.: US 11,358,977 B2
(45) Date of Patent: Jun. 14, 2022

(54) DEUTERATED PYRIDONE AMIDES AND PRODRUGS THEREOF AS MODULATORS OF SODIUM CHANNELS

(71) Applicant: VERTEX PHARMACEUTICALS INCORPORATED, Boston, MA (US)

(72) Inventors: Licong Jiang, San Diego, CA (US); Sara Sabina Hadida Ruah, La Jolla, CA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 31 days.

(21) Appl. No.: 16/614,015

(22) PCT Filed: May 16, 2018

(86) PCT No.: PCT/US2018/032939
§ 371 (c)(1),
(2) Date: Nov. 15, 2019

(87) PCT Pub. No.: WO2018/213426
PCT Pub. Date: Nov. 22, 2018

(65) Prior Publication Data
US 2021/0155643 A1 May 27, 2021

Related U.S. Application Data

(60) Provisional application No. 62/507,172, filed on May 16, 2017, provisional application No. 62/547,718, filed on Aug. 18, 2017.

(51) Int. Cl.
*C07D 213/75* (2006.01)
*C07F 9/58* (2006.01)
*C07B 59/00* (2006.01)

(52) U.S. Cl.
CPC .............. *C07F 9/58* (2013.01); *C07B 59/002* (2013.01); *C07D 213/75* (2013.01); *C07B 2200/05* (2013.01)

(58) Field of Classification Search
CPC ..... C07D 213/75; C07F 9/58; C07B 2200/05; C07B 59/002
See application file for complete search history.

(56) References Cited

U.S. PATENT DOCUMENTS

| | | | |
|---|---|---|---|
| 5,304,121 A | 4/1994 | Sahatjian | |
| 5,886,026 A | 3/1999 | Hunter et al. | |
| 6,099,562 A | 8/2000 | Ding et al. | |
| 6,221,335 B1* | 4/2001 | Foster | C07B 59/002 424/1.81 |
| 6,440,710 B1* | 8/2002 | Keinan | C12P 13/02 435/147 |
| 6,603,008 B1* | 8/2003 | Ando | A61P 25/00 546/269.7 |
| 7,517,990 B2* | 4/2009 | Ito | C07D 213/16 546/184 |
| 8,389,734 B2 | 3/2013 | Chen | |
| 8,466,188 B2 | 6/2013 | Chafeev et al. | |
| 8,486,950 B2 | 7/2013 | Goodacre et al. | |
| 8,519,137 B2 | 8/2013 | Joshi | |
| 8,779,197 B2 | 7/2014 | Chen | |
| 8,841,483 B2 | 9/2014 | Joshi | |
| 8,865,771 B2 | 10/2014 | Chen | |
| 8,883,840 B2 | 11/2014 | Chafeev et al. | |

(Continued)

FOREIGN PATENT DOCUMENTS

| | | |
|---|---|---|
| CN | 101855210 | 10/2010 |
| CN | 101883758 | 11/2010 |

(Continued)

OTHER PUBLICATIONS

Dyck et al., Journal of Neurochemistry vol. 46, Issue 2, pp. 399-404 (1986). (Year: 1986).*

(Continued)

*Primary Examiner* — Laura L Stockton
(74) *Attorney, Agent, or Firm* — Barnes & Thornburg LLP

(57) ABSTRACT

Compounds, and pharmaceutically acceptable salts thereof, useful as inhibitors of sodium channels are provided. The compounds have the formula (I) wherein R is H or CH$_2$OPO (OH)$_2$. Also provided are pharmaceutical compositions comprising the compounds or pharmaceutically acceptable salts and methods of using the compounds, pharmaceutically acceptable salts, and pharmaceutical compositions in the treatment of various disorders, including pain.

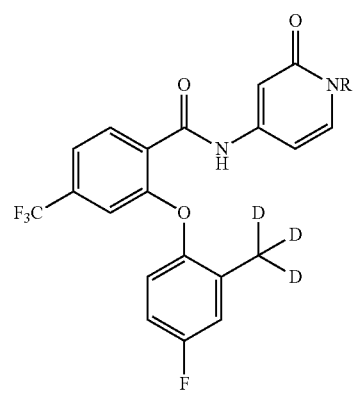

20 Claims, 3 Drawing Sheets

(56) References Cited

U.S. PATENT DOCUMENTS

| | | | |
|---|---|---|---|
| 9,051,270 | B2 | 6/2015 | Hadida Ruah |
| 9,108,903 | B2 | 8/2015 | Hadida Ruah |
| 9,139,529 | B2 | 9/2015 | Hadida Ruah |
| 9,163,008 | B2 | 10/2015 | Ni et al. |
| 9,163,042 | B2 | 10/2015 | Anderson |
| 9,393,235 | B2 | 7/2016 | Hadida Ruah |
| 9,421,196 | B2 | 8/2016 | Hadida Ruah |
| 9,464,102 | B2 | 10/2016 | Anderson |
| 9,656,959 | B2 | 5/2017 | Ni et al. |
| 9,758,483 | B2 | 9/2017 | Hadida Ruah |
| 9,783,501 | B2 | 10/2017 | Hadida Ruah |
| 9,828,397 | B2 | 11/2017 | Anderson |
| 10,087,143 | B2 | 10/2018 | Hadida Ruah et al. |
| 10,253,054 | B2 | 4/2019 | Anderson et al. |
| 10,647,661 | B2 | 5/2020 | Ahmad et al. |
| 2007/0082929 | A1* | 4/2007 | Gant .................. A61P 1/00 514/338 |
| 2007/0197695 | A1* | 8/2007 | Potyen .................. C08K 5/55 524/110 |
| 2007/0238733 | A1 | 10/2007 | Joshi |
| 2009/0099233 | A1 | 4/2009 | Joshi |
| 2009/0118333 | A1 | 5/2009 | Chen |
| 2009/0118338 | A1 | 5/2009 | Chen |
| 2010/0105906 | A1 | 4/2010 | Bissantz et al. |
| 2013/0231370 | A1 | 9/2013 | Chen |
| 2013/0303535 | A1 | 11/2013 | Tsuboi et al. |
| 2014/0213616 | A1 | 7/2014 | Hadida Ruah |
| 2014/0221435 | A1 | 8/2014 | Hadida Ruah |
| 2014/0228371 | A1 | 8/2014 | Hadida Ruah |
| 2015/0166589 | A1 | 6/2015 | Anderson |
| 2015/0246028 | A1 | 9/2015 | Hadida Ruah |
| 2015/0328196 | A1 | 11/2015 | Hadida Ruah |
| 2015/0336945 | A1 | 11/2015 | Hadida Ruah |
| 2015/0376174 | A1 | 12/2015 | Kawana et al. |
| 2016/0009743 | A1 | 1/2016 | Anderson |
| 2016/0152561 | A1 | 6/2016 | Hadida Ruah |
| 2016/0376295 | A1 | 12/2016 | Anderson |
| 2017/0037009 | A1 | 2/2017 | Hadida Ruah |
| 2018/0016235 | A1 | 1/2018 | Hadida Ruah |
| 2018/0044361 | A1 | 2/2018 | Anderson |
| 2019/0016671 | A1 | 1/2019 | Ahmad |
| 2019/0248745 | A1 | 8/2019 | Seaman |
| 2019/0276483 | A1 | 9/2019 | Northington |
| 2019/0343817 | A1 | 11/2019 | Chandrakumar |

FOREIGN PATENT DOCUMENTS

| | | |
|---|---|---|
| CN | 102264722 | 11/2011 |
| CN | 103429571 | 12/2013 |
| JP | 2003/034671 | 2/2003 |
| JP | 2005/531501 | 10/2005 |
| JP | 2011/500599 | 1/2011 |
| JP | 2011/500600 | 1/2011 |
| JP | 2012/506887 | 3/2012 |
| JP | 2016/506963 | 3/2016 |
| JP | 2016/508500 | 3/2016 |
| JP | 2016/525122 | 8/2016 |
| RU | 2010/118467 | 11/2011 |
| RU | 2010/118481 | 11/2011 |
| TW | 2013/31186 | 8/2013 |
| WO | WO 2002/008748 | 1/2002 |
| WO | WO 2003/068230 | 8/2003 |
| WO | WO 2005/013914 | 2/2005 |
| WO | WO 2006/011050 | 2/2006 |
| WO | WO 2007/120647 | 10/2007 |
| WO | WO 2008/135826 | 11/2008 |
| WO | WO 2009/049181 | 4/2009 |
| WO | WO 2009/049183 | 4/2009 |
| WO | WO 2010/072607 | 7/2010 |
| WO | WO 2010/137351 | 12/2010 |
| WO | WO 2011/026240 | 3/2011 |
| WO | WO 2011/140425 | 11/2011 |
| WO | WO 2012/106499 | 8/2012 |
| WO | WO 2012/112743 | 8/2012 |
| WO | WO 2012/116440 | 9/2012 |
| WO | WO 2012/119006 | 9/2012 |
| WO | WO 2012/125613 | 9/2012 |
| WO | WO 2013/061205 | 5/2013 |
| WO | WO 2013/109521 | 7/2013 |
| WO | WO 2013/114250 | 8/2013 |
| WO | WO 2013/131018 | 9/2013 |
| WO | WO 2013/132376 | 9/2013 |
| WO | WO 2014/120808 | 8/2014 |
| WO | WO 2014/120815 | 8/2014 |
| WO | WO 2014/120820 | 8/2014 |
| WO | WO 2015/010065 | 1/2015 |
| WO | WO 2015/089361 | 6/2015 |

OTHER PUBLICATIONS

Tonn et al., Biological Mass Spectrometry vol. 22, Issue 11, pp. 633-642 (1993). (Year: 1993).*
Haskins, Biomedical Mass Spectrometry, vol. 9 No. 7, pp. 269-277 (1982). (Year: 1982).*
Wolen, Journal of Clinical Pharmacology, 1986, vol. 26, pp. 419-424. (Year: 1986).*
Browne, Journal of Clinical Pharmacology, 1998; vol. 38, pp. 213-220. (Year: 1998).*
Baillie, Pharmacology Reviews, 1981, vol. 33, No. 2, pp. 81-132. (Year: 1981).*
Gouyette, Biomedical and Environmental Mass Spectrometry, vol. 15, pp. 243-247 (1988). (Year: 1988).*
Cherrah et al., Biomedical and Environmental Mass Spectrometry, vol. 14, Issue 11, pp. 653-657 (1987). (Year: 1987).*
Pieniaszek et al., Journal of Clinical Pharmacology, 1999, vol. 39, pp. 817-825. (Year: 1999).*
Honma et al., Drug Metabolism and Disposition, vol. 15, No. 4, pp. 551-559 (1987). (Year: 1987).*
Akopian, A.N., L. Sivilotti, and J.N. Wood, A tetrodotoxin-resistant voltage-gated sodium channel expressed by sensory neurons. *Nature*, 1996. 379(6562): p. 257-62.
Black, J.A., et al., Multiple sodium channel isoforms and mitogen-activated protein kinases are present in painful human neuromas. *Ann Neurol*, 2008. 64(6): p. 644-53.
Blair, N.T. and B.P. Bean, Roles of tetrodotoxin (TTX)-sensitive $Na^+$current, TTX-resistant $Na^+$current, and $Ca^{2+}$current in the action potentials of nociceptive sensory neurons. *J Neurosci.*, 2002. 22(23): p. 10277-90.
CAS Registry No. 1119379-37-1 (Mar. 12, 2009).
CAS Registry No. 1223014-19-4 (May 13, 2010).
CAS Registry No. 1241310-16-6 (Sep. 15, 2010).
CAS Registry No. 1252156-94-7 (Nov. 9, 2010).
CAS Registry No. 1258714-13-4 (Jan. 7, 2011).
CAS Registry No. 1258742-89-0 (Jan. 7, 2011).
CAS Registry No. 1281024-95-0 (Apr. 17, 2011).
CAS Registry No. 1281059-52-6 (Apr. 17, 2011).
CAS Registry No. 1281112-60-4 (Apr. 17, 2011).
CAS Registry No. 1287712-50-8 (Apr. 29, 2011).
CAS Registry No. 1301902-75-9 (May 29, 2011).
CAS Registry No. 1311734-41-4 (Jul. 7, 2011).
CAS Registry No. 1394673-41-6 (Sep. 18, 2012).
CAS Registry No. 1394698-15-7 (Sep. 18, 2012).
Catterall, W. A., Goldin, A. L., and Waxman, S. G., International Union of Pharmacology. XLVII. Nomenclature and structure-function relationships of voltage-gated sodium channels. *Pharmacol Rev* 57 (4), p. 397 (2005).
Chahine, M., Chatelier, A., Babich, O., and Krupp, J. J., Voltage-gated sodium channels in neurological disorders. *CNS Neurol Disord Drug Targets* 7 (2), p. 144-58 (2008).
Choi, J.S. and S.G. Waxman, Physiological interactions between $Na_v1.7$ and $Na_v1.8$ sodium channels: a computer simulation study. *J Neurophysiol.* 106(6): p. 3173-84; 2011.
Coward, K., et al., Immunolocalization of SNS/PN3 and NaN/SNS2 sodium channels in human pain states. *Pain*, 2000. 85(1-2): p. 41-50.

(56) References Cited

OTHER PUBLICATIONS

Dieleman, J.P., et al., Incidence rates and treatment of neuropathic pain conditions in the general population. *Pain*, 2008. 137(3): p. 681-8.

Dong, X.W., et al., Small interfering RNA-mediated selective knockdown of Na$_{(v)}$1.8 tetrodotoxin-resistant sodium channel reverses mechanical allodynia in neuropathic rats. *Neuroscience*, 2007. 146(2): p. 812-21.

England, S., Voltage-gated sodium channels: the search for subtype-selective analgesics. *Expert Opin Investig Drugs* 17 (12), p. 1849-64 (2008).

Gant, T.G., Using Deuterium in Drug Discovery: Leaving the Label in the Drug, Journal of Medicinal Chemistry, vol. 57, No. 9, (May 2014), pp. 3599.

Huang, H.L., et al., Proteomic profiling of neuromas reveals alterations in protein composition and local protein synthesis in hyperexcitable nerves. *Mol Pain*, 2008. 4: p. 33.

International Search Report and Written Opinion of the International Searching Authority for International Application No. PCT/US2014/069916 (dated Feb. 12, 2015).

International Search Report and Written Opinion of the International Searching Authority for International Application No. PCT/US2014/013652 (dated Apr. 2, 2014).

International Search Report and Written Opinion of the International Searching Authority for International Application No. PCT/US2018/032939 (dated Aug. 7, 2018).

Jarvis, M.F., et al., A-803467, a potent and selective Na$_v$1.8 sodium channel blocker, attenuates neuropathic and inflammatory pain in the rat. *Proc Natl Acad Sci. U S A*, 2007. 104(20): p. 8520-5.

Joshi, S.K., et al., Involvement of the TTX-resistant sodium channel Nav1.8 in inflammatory and neuropathic, but not post-operative, pain states. *Pain*, 2006. 123(1-2): pp. 75-82.

Krafte, D. S. and Bannon, A. W., Sodium channels and nociception: recent concepts and therapeutic opportunities. *Curr Opin Pharmacol* 8 (1), p. 50-56 (2008).

Lai, J., et al., Inhibition of neuropathic pain by decreased expression of the tetrodotoxin-resistant sodium channel, Na$_v$1.8. *Pain*, 2002. 95(1-2): p. 143-52.

Qiu, F., et al., Increased expression of tetrodotoxin-resistant sodium channels Na$_v$1.8 and Na$_v$1.9 within dorsal root ganglia in a rat model of bone cancer pain. *Neurosci. Lett.* 512(2): p. 61-6), 2012.

Renganathan, M., T.R. Cummins, and S.G. Waxman, Contribution of Na$_{(v)}$1.8 sodium channels to action potential electrogenesis in DRG neurons. *J Neurophysiol.*, 2001. 86(2): p. 629-40.

Roza, C., et al., The tetrodotoxin-resistant Na$^+$channel Na$_v$1.8 is essential for the expression of spontaneous activity in damaged sensory axons of mice. *J. Physiol.*, 2003. 550(Pt 3): p. 921-6.

Ruangsri, S., et al., Relationship of axonal voltage-gated sodium channel 1.8 (Na$_v$1.8) mRNA accumulation to sciatic nerve injury-induced painful neuropathy in rats. *J Biol Chem.* 286(46): p. 39836-47; 2011.

Rush, A.M. and T.R. Cummins, *Painful Research: Identification of a Small-Molecule Inhibitor that Selectively Targets Na$_v$1.8 Sodium Channels*. Mol Interv, 2007. 7(4): p. 192-5).

Rush, A.M., et al., A single sodium channel mutation produces hyper- or hypoexcitability in different types of neurons. *Proc Natl Acad Sci USA*, 2006. 103(21): p. 8245-50.

Soderpalm, B., Anticonvulsants: aspects of their mechanisms of action. *Eur J Pain* 6 Suppl A, p. 3-9(2002).

Strickland, I.T., et al., Changes in the expression of NaV1.7, Na$_v$1.8 and Na$_v$1.9 in a distinct population of dorsal root ganglia innervating the rat knee joint in a model of chronic inflammatory joint pain. *Eur J Pain*, 2008. 12(5): p. 564-72.

Sun, W., et al., Reduced conduction failure of the main axon of polymodal nociceptive C-fibres contributes to painful diabetic neuropathy in rats. *Brain*. 135(Pt 2): p. 359-75, 2012.

Wang, G. K., Mitchell, J., and Wang, S. Y., Block of persistent late Na$^+$currents by antidepressant sertraline and paroxetine. *J Membr Biol* 222 (2), p. 79-90 (2008).

Yiangou, Y., et al., SNS/PN3 and SNS2/NaN sodium channel-like immunoreactivity in human adult and neonate injured sensory nerves. *FEBS Lett*, 2000. 467(2-3): p. 249-52.

Halford, Bethany, "Deuterium switcheroo breathes life into old drugs," *Drug Development*, vol. 94, Iss. 27, pp. 1-13 (Jul. 4, 2016).

* cited by examiner

DEUTERATED PYRIDONE AMIDES AND PRODRUGS THEREOF AS MODULATORS OF SODIUM CHANNELS

CROSS REFERENCE TO RELATED APPLICATIONS

This application claims the benefit of U.S. Provisional Application No. 62/507,172, filed May 16, 2017, and U.S. Provisional Application No. 62/547,718, filed Aug. 18, 2017, both of which are incorporated by reference in their entirety.

BACKGROUND

Pain is a protective mechanism that allows healthy animals to avoid tissue damage and to prevent further damage to injured tissue. Nonetheless there are many conditions where pain persists beyond its usefulness, or where patients would benefit from inhibition of pain. Neuropathic pain is a form of chronic pain caused by an injury to the sensory nerves (Dieleman, J P, et al., Incidence rates and treatment of neuropathic pain conditions in the general population. *Pain*, 2008. 137(3): p. 681-8). Neuropathic pain can be divided into two categories, pain caused by generalized metabolic damage to the nerve and pain caused by a discrete nerve injury. The metabolic neuropathies include post herpetic neuropathy, diabetic neuropathy, and drug-induced neuropathy. Discrete nerve injuries indications include post amputation pain, post-surgical nerve injury pain, and nerve entrapment injuries like neuropathic back pain.

Voltage-gated sodium channels ($Na_V$'s) are involved in pain signaling $Na_V$'s are biological mediators of electrical signaling as they mediate the rapid upstroke of the action potential of many excitable cell types (e.g. neurons, skeletal myocytes, cardiac myocytes). The evidence for the role of these channels in normal physiology, the pathological states arising from mutations in sodium channel genes, preclinical work in animal models, and the clinical pharmacology of known sodium channel modulating agents all point to the central role of $Na_V$'s in pain sensation (Rush, A. M. and T. R. Cummins, *Painful Research: Identification of a Small-Molecule Inhibitor that Selectively Targets $Na_V$1.8 Sodium Channels*. Mol Interv, 2007. 7(4): p. 192-5); England, S., Voltage-gated sodium channels: the search for subtype-selective analgesics. *Expert Opin Investig Drugs* 17 (12), p. 1849-64 (2008); Krafte, D. S. and Bannon, A. W., Sodium channels and nociception: recent concepts and therapeutic opportunities. *Curr Opin Pharmacol* 8 (1), p. 50-56 (2008)). $Na_V$'s mediate the rapid upstroke of the action potential of many excitable cell types (e.g. neurons, skeletal myocytes, cardiac myocytes), and thus are involved in the initiation of signaling in those cells (Hille, Bertil, *Ion Channels of Excitable Membranes*, Third ed. (Sinauer Associates, Inc., Sunderland, Mass., 2001)). Because of the role $Na_V$'s play in the initiation and propagation of neuronal signals, antagonists that reduce $Na_V$ currents can prevent or reduce neural signaling and $Na_V$ channels have been considered likely targets to reduce pain in conditions where hyper-excitability is observed (Chahine, M., Chatelier, A., Babich, O., and Krupp, J. J., Voltage-gated sodium channels in neurological disorders. *CNS Neurol Disord Drug Targets* 7 (2), p. 144-58 (2008)). Several clinically useful analgesics have been identified as inhibitors of $Na_V$ channels. The local anesthetic drugs such as lidocaine block pain by inhibiting $Na_V$ channels, and other compounds, such as carbamazepine, lamotrigine, and tricyclic antidepressants that have proven effective at reducing pain have also been suggested to act by sodium channel inhibition (Soderpalm, B., Anticonvulsants: aspects of their mechanisms of action. *Eur J Pain* 6 Suppl A, p. 3-9 (2002); Wang, G. K., Mitchell, J., and Wang, S. Y., Block of persistent late $Na^+$ currents by antidepressant sertraline and paroxetine. *J Membr Biol* 222 (2), p. 79-90 (2008)).

The $Na_V$'s form a subfamily of the voltage-gated ion channel super-family and comprises 9 isoforms, designated $Na_V1.1$-$Na_V1.9$. The tissue localizations of the nine isoforms vary. $Na_V1.4$ is the primary sodium channel of skeletal muscle, and $Na_V1.5$ is primary sodium channel of cardiac myocytes. $Na_V$'s 1.7, 1.8 and 1.9 are primarily localized to the peripheral nervous system, while $Na_V$'s 1.1, 1.2, 1.3, and 1.6 are neuronal channels found in both the central and peripheral nervous systems. The functional behaviors of the nine isoforms are similar but distinct in the specifics of their voltage-dependent and kinetic behavior (Catterall, W. A., Goldin, A. L., and Waxman, S. G., International Union of Pharmacology. XLVII. Nomenclature and structure-function relationships of voltage-gated sodium channels. *Pharmacol Rev* 57 (4), p. 397 (2005)).

Upon their discovery, $Na_V1.8$ channels were identified as likely targets for analgesia (Akopian, A. N., L. Sivilotti, and J. N. Wood, A tetrodotoxin-resistant voltage-gated sodium channel expressed by sensory neurons. *Nature*, 1996. 379 (6562): p. 257-62). Since then, $Na_V1.8$ has been shown to be a carrier of the sodium current that maintains action potential firing in small DRG neurons (Blair, N. T. and B. P. Bean, Roles of tetrodotoxin (TTX)-sensitive Na+ current, TTX-resistant $Na^+$ current, and $Ca^{2+}$ current in the action potentials of nociceptive sensory neurons. *J Neurosci.*, 2002. 22(23): p. 10277-90). $Na_V1.8$ is involved in spontaneous firing in damaged neurons, like those that drive neuropathic pain (Roza, C., et al., The tetrodotoxin-resistant Na channel $Na_V1.8$ is essential for the expression of spontaneous activity in damaged sensory axons of mice. *J. Physiol.*, 2003. 550(Pt 3): p. 921-6; Jarvis, M. F., et al., A-803467, a potent and selective $Na_V1.8$ sodium channel blocker, attenuates neuropathic and inflammatory pain in the rat. *Proc Natl Acad Sci. USA*, 2007. 104(20): p. 8520-5; Joshi, S. K., et al., Involvement of the TTX-resistant sodium channel Nav1.8 in inflammatory and neuropathic, but not post-operative, pain states. *Pain*, 2006. 123(1-2): pp. 75-82; Lai, J., et al., Inhibition of neuropathic pain by decreased expression of the tetrodotoxin-resistant sodium channel, $Na_V1.8$. *Pain*, 2002. 95(1-2): p. 143-52; Dong, X. W., et al., Small interfering RNA-mediated selective knockdown of $Na_{(V)}1.8$ tetrodotoxin-resistant sodium channel reverses mechanical allodynia in neuropathic rats. *Neuroscience*, 2007. 146(2): p. 812-21; Huang, H. L., et al., Proteomic profiling of neuromas reveals alterations in protein composition and local protein synthesis in hyper-excitable nerves. *Mol Pain*, 2008. 4: p. 33; Black, J. A., et al., Multiple sodium channel isoforms and mitogen-activated protein kinases are present in painful human neuromas. *Ann Neurol*, 2008. 64(6): p. 644-53; Coward, K., et al., Immunolocalization of SNS/PN3 and NaN/SNS2 sodium channels in human pain states. *Pain*, 2000. 85(1-2): p. 41-50; Yiangou, Y., et al., SNS/PN3 and SNS2/NaN sodium channel-like immunoreactivity in human adult and neonate injured sensory nerves. *FEBS Lett*, 2000.

467(2-3): p. 249-52; Ruangsri, S., et al., Relationship of axonal voltage-gated sodium channel 1.8 (Na$_V$1.8) mRNA accumulation to sciatic nerve injury-induced painful neuropathy in rats. *J Biol Chem.* 286(46): p. 39836-47). The small DRG neurons where Na$_V$1.8 is expressed include the nociceptors involved in pain signaling Na$_V$1.8 mediates large amplitude action potentials in small neurons of the dorsal root ganglia (Blair, N. T. and B. P. Bean, Roles of tetrodotoxin (TTX)-sensitive Na$^+$ current, TTX-resistant Na current, and Ca$^{2+}$ current in the action potentials of nociceptive sensory neurons. *J Neurosci.*, 2002. 22(23): p. 10277-90). Na$_V$1.8 is necessary for rapid repetitive action potentials in nociceptors, and for spontaneous activity of damaged neurons. (Choi, J. S. and S. G. Waxman, Physiological interactions between Na$_V$1.7 and Na$_V$1.8 sodium channels: a computer simulation study. *J Neurophysiol.* 106(6): p. 3173-84; Renganathan, M., T. R. Cummins, and S. G. Waxman, Contribution of Na$_{(V)}$1.8 sodium channels to action potential electrogenesis in DRG neurons. *J Neurophysiol.*, 2001. 86(2): p. 629-40; Roza, C., et al., The tetrodotoxin-resistant Na$^+$ channel Na$_V$1.8 is essential for the expression of spontaneous activity in damaged sensory axons of mice. *J Physiol.*, 2003. 550(Pt 3): p. 921-6). In depolarized or damaged DRG neurons, Na$_V$1.8 appears to be a driver of hyper-excitablility (Rush, A. M., et al., A single sodium channel mutation produces hyper- or hypoexcitability in different types of neurons. *Proc Natl Acad Sci USA*, 2006. 103(21): p. 8245-50). In some animal pain models, Na$_V$1.8 mRNA expression levels have been shown to increase in the DRG (Sun, W., et al., Reduced conduction failure of the main axon of polymodal nociceptive C-fibers contributes to painful diabetic neuropathy in rats. *Brain.* 135(Pt 2): p. 359-75; Strickland, I. T., et al., Changes in the expression of NaV1.7, Na$_V$1.8 and Na$_V$1.9 in a distinct population of dorsal root ganglia innervating the rat knee joint in a model of chronic inflammatory joint pain. *Eur J Pain*, 2008. 12(5): p. 564-72; Qiu, F., et al., Increased expression of tetrodotoxin-resistant sodium channels Na$_V$1.8 and Na$_V$1.9 within dorsal root ganglia in a rat model of bone cancer pain. *Neurosci. Lett.* 512(2): p. 61-6).

The primary drawback to some known Na$_V$ inhibitors is their poor therapeutic window, and this is likely a consequence of their lack of isoform selectivity. Since Na$_V$1.8 is primarily restricted to the neurons that sense pain, selective Na$_V$1.8 blockers are unlikely to induce the adverse events common to non-selective Na$_V$ blockers. Accordingly, there remains a need to develop additional Na$_V$ channel modulators, preferably those that are more potent and selective for Nav1.8, with increased metabolic stability, increased solubility, and with fewer side effects.

A class of pyridone amide compounds useful as inhibitors of Na$_v$1.8 sodium channels was described in International Publication No. WO 2014/120808 A9 and US Publication No. 2014/0213616 A1, and prodrugs of these compounds were described in International Publication No. WO 2015/089361 A1 and US Publication No. 2015/0166589 A1, all of which are incorporated by reference in their entirety. Those pyridone amide compounds address some of the drawbacks of prior Na$_v$18 inhibitors, but further improvements may still be made.

SUMMARY

In one aspect, the invention relates to a compound of formula I:

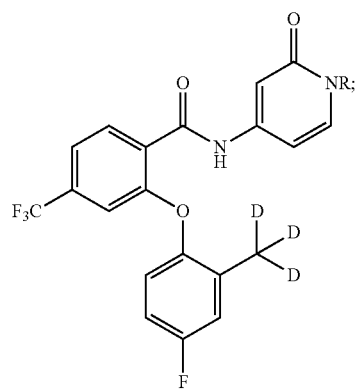 [SMILES: [2H]C([2H])([2H])c1cc(F)ccc1Oc1cc(C(F)(F)F)ccc1C(=O)Nc1cc[nH]c(=O)c1]

or a pharmaceutically acceptable salt thereof, wherein R is H or CH$_2$OPO(OH)$_2$.

In another aspect, the invention relates to a compound of formula I that is

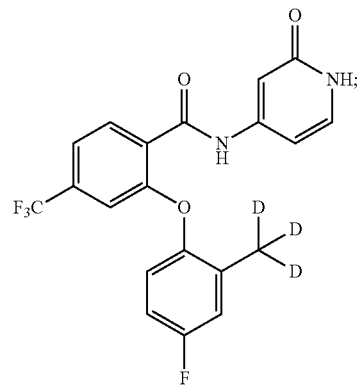

or a pharmaceutically acceptable salt thereof.

In another aspect, the invention relates to a compound of formula I that is

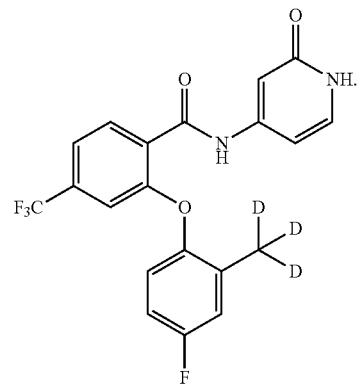 [SMILES: [2H]C([2H])([2H])c1cc(F)ccc1Oc1cc(C(F)(F)F)ccc1C(=O)Nc1cc[nH]c(=O)c1]

In another aspect, the invention relates to a compound of formula I that is

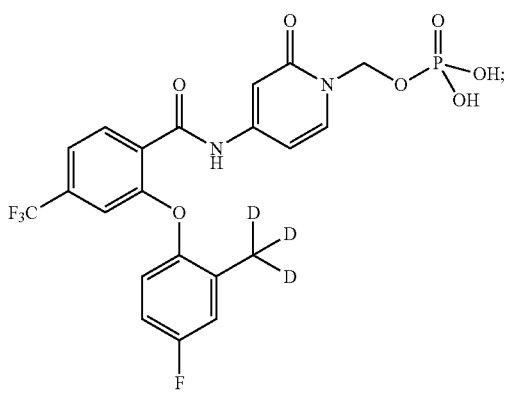 [SMILES: [2H]C([2H])([2H])c1cc(F)ccc1Oc1cc(C(F)(F)F)ccc1C(=O)Nc1ccn(COP(=O)(O)O)c(=O)c1]

or a pharmaceutically acceptable salt thereof.

In another aspect, the invention relates to a compound of formula I that is

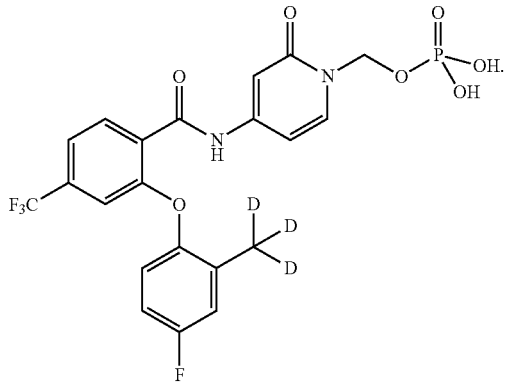 [SMILES: [2H]C([2H])([2H])c1cc(F)ccc1Oc1cc(C(F)(F)F)ccc1C(=O)Nc1ccn(COP(=O)(O)O)c(=O)c1]

In another aspect, the invention relates to a pharmaceutical composition comprising the compound of formula I, or a pharmaceutically acceptable salt thereof, and one or more pharmaceutically acceptable carriers or vehicles.

In still another aspect, the invention relates to a method of inhibiting a voltage gated sodium channel in a subject by administering the compound of formula I, pharmaceutically acceptable salt, or pharmaceutical composition to the subject.

In yet another aspect, the invention relates to a method of treating or lessening the severity in a subject of a variety of diseases, disorders, or conditions, including, but not limited to, chronic pain, gut pain, neuropathic pain, musculoskeletal pain, acute pain, inflammatory pain, cancer pain, idiopathic pain, postsurgical pain (e.g., bunionectomy pain or abdominoplasty pain), visceral pain, multiple sclerosis, Charcot-Marie-Tooth syndrome, incontinence, pathological cough, and cardiac arrhythmia, by administering the compound of formula I, pharmaceutically acceptable salt, or pharmaceutical composition to the subject.

DETAILED DESCRIPTION

Figure 1:
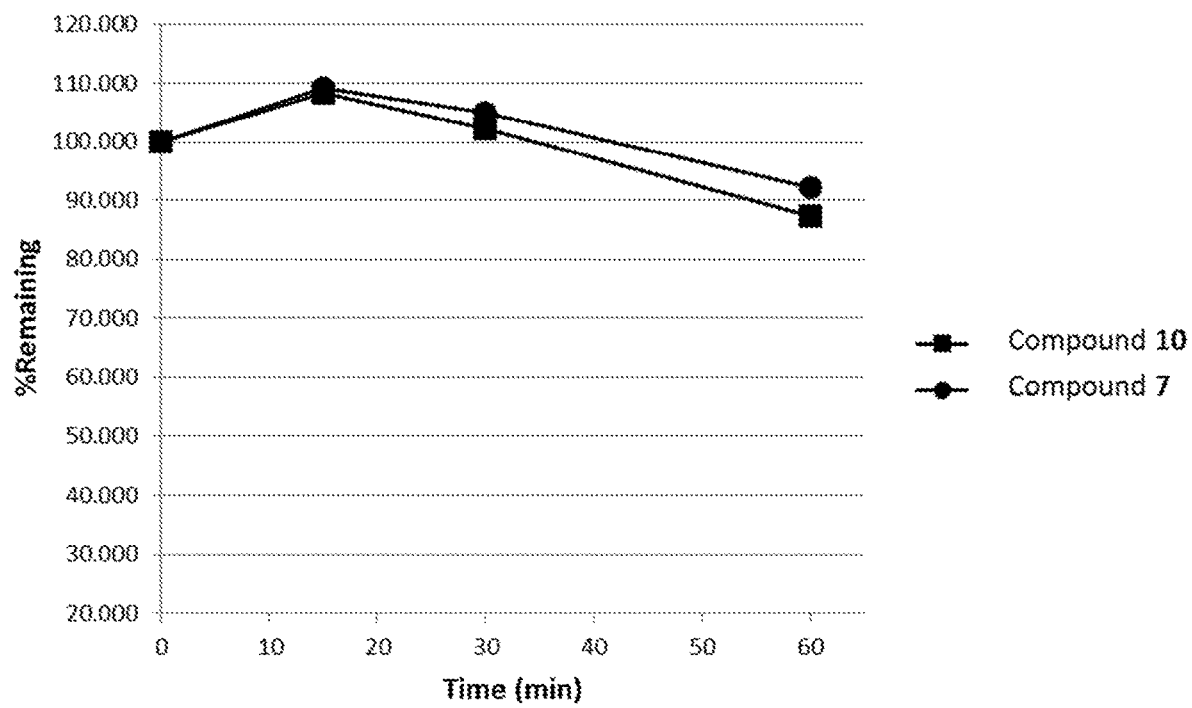
FIG. 1 is a plot of the percentage of Compounds 7 and 10 remaining over time during incubation in the presence of rat liver microsomes.
Figure 2:
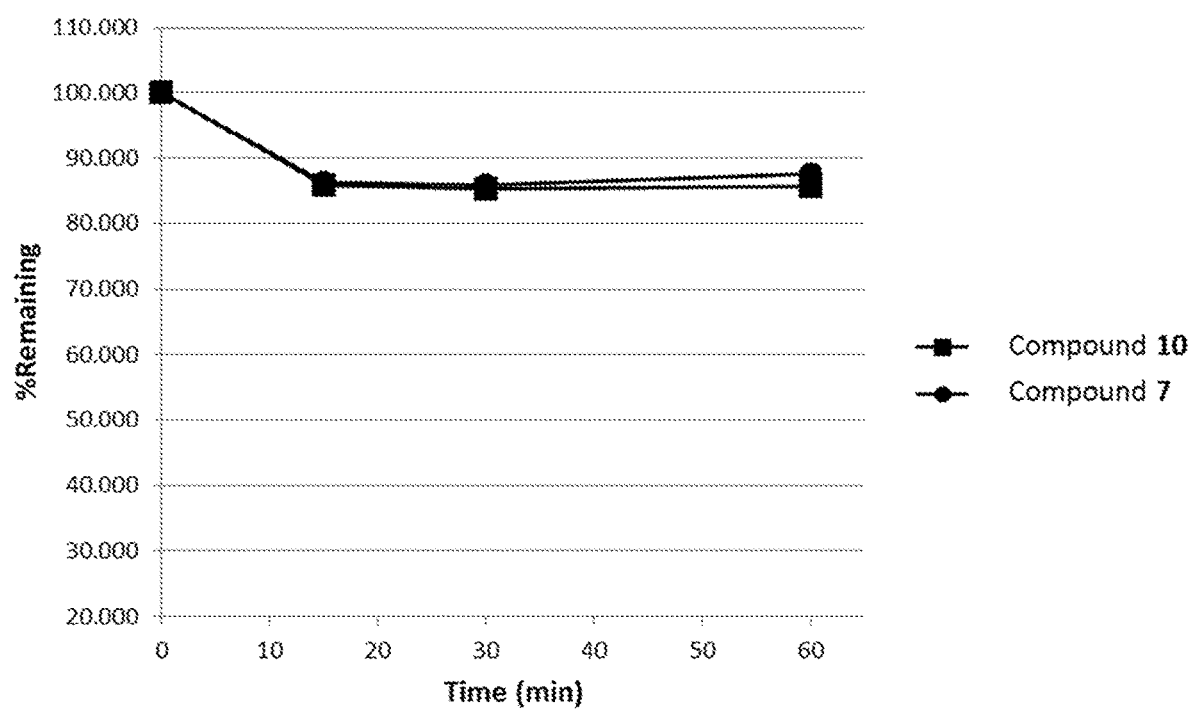
FIG. 2 is a plot of the percentage of Compounds 7 and 10 remaining over time during incubation in the presence of dog liver microsomes.
Figure 3:
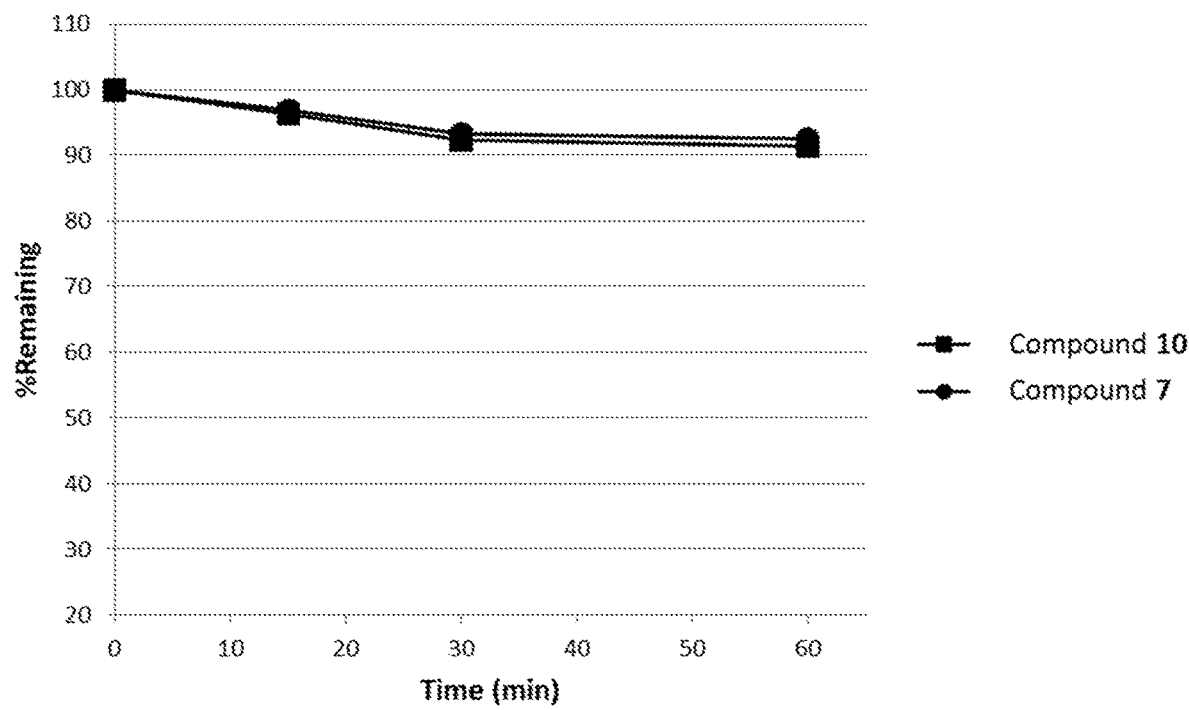
FIG. 3 is a plot of the percentage of Compounds 7 and 10 remaining over time during incubation in the presence of monkey liver microsomes.
Figure 4:
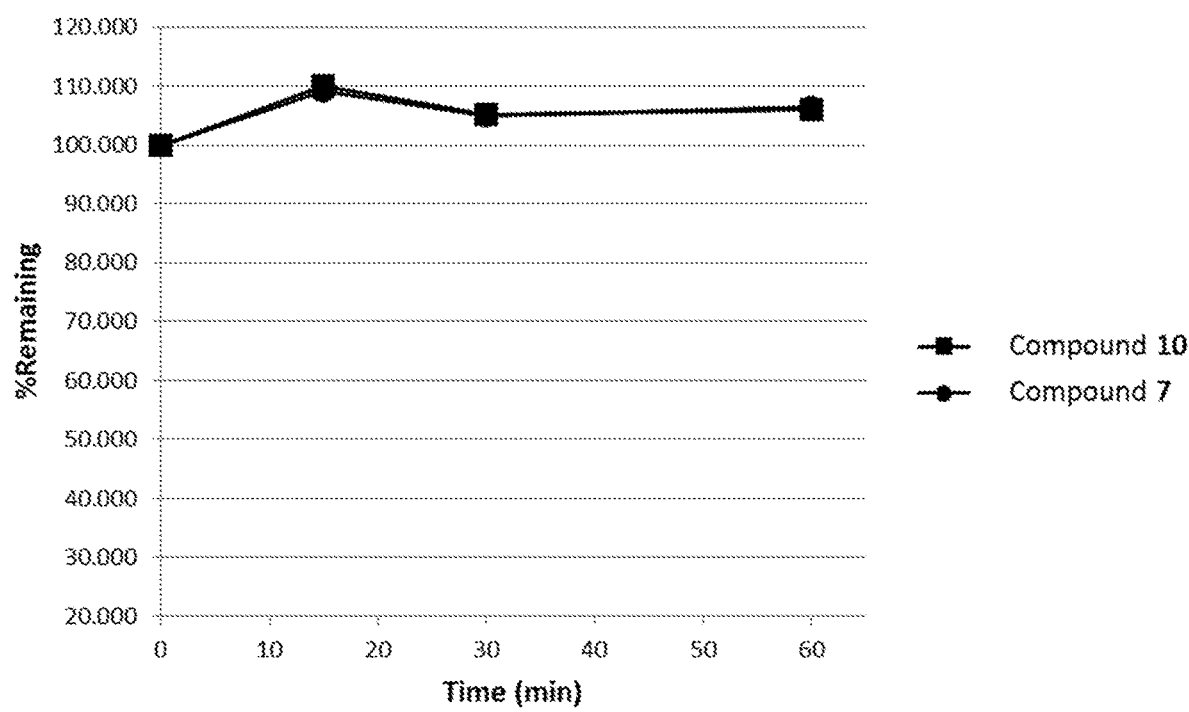
FIG. 4 is a plot of the percentage of Compounds 7 and 10 remaining over time during incubation in the presence of human liver microsomes.

In one aspect, the invention relates to a compound of formula I:

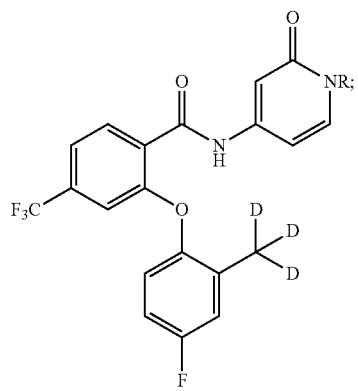 [SMILES: [2H]C([2H])([2H])c1cc(F)ccc1Oc1cc(C(F)(F)F)ccc1C(=O)Nc1cc[nH]c(=O)c1]

or a pharmaceutically acceptable salt thereof, wherein R is H or $CH_2OPO(OH)_2$.

In another aspect, the invention relates to a compound of formula I that is

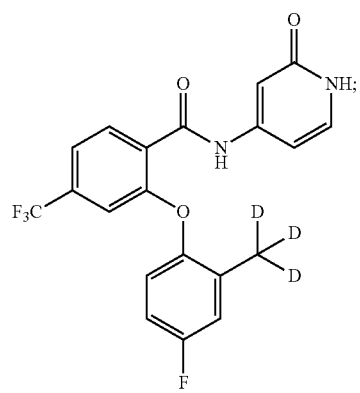 [SMILES: [2H]C([2H])([2H])c1cc(F)ccc1Oc1cc(C(F)(F)F)ccc1C(=O)Nc1cc[nH]c(=O)c1]

or a pharmaceutically acceptable salt thereof.

In another aspect, the invention relates to a compound of formula I that is

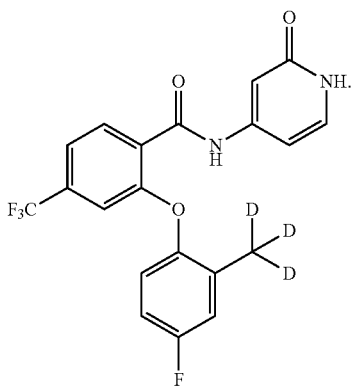

In another aspect, the invention relates to a compound of formula I that is

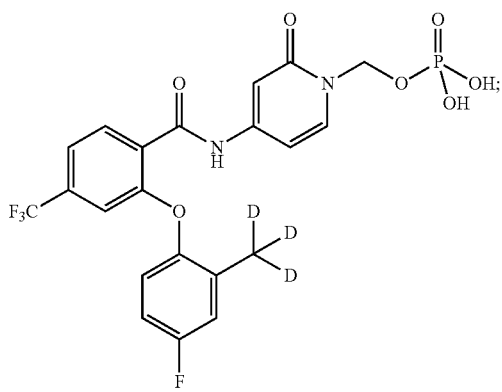 [SMILES: [2H]C([2H])([2H])c1cc(F)ccc1Oc1cc(C(F)(F)F)ccc1C(=O)Nc1ccn(COP(=O)(O)O)c(=O)c1]

or a pharmaceutically acceptable salt thereof.

In another aspect, the invention relates to a compound of formula I that is

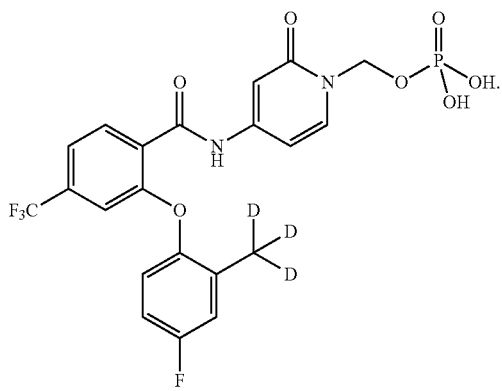 [SMILES: [2H]C([2H])([2H])c1cc(F)ccc1Oc1cc(C(F)(F)F)ccc1C(=O)Nc1ccn(COP(=O)(O)O)c(=O)c1]

The compound of formula I in which R is $CH_2OPO(OH)_2$, and pharmaceutically acceptable salts thereof, are prodrugs of the parent compound in which R is H.

As used herein, the term "prodrug" refers to compounds and salts which are drug precursors which, following administration and absorption, release the drug in vivo via some metabolic process. In general, a prodrug possesses less biological activity than its parent drug. A prodrug may also improve the physical properties of the parent drug and/or it may improve overall drug efficacy, for example through the reduction of toxicity and unwanted effects of a drug by controlling its absorption, blood levels, metabolic distribution and cellular uptake.

As used herein, the term "parent compound" or "parent drug" refers to the biologically active entity that is released via enzymatic action of a metabolic or a catabolic process, or via a chemical process following administration of the prodrug. The parent compound may also be the starting material for the preparation of its corresponding prodrug.

For purposes of this invention, the chemical elements are identified in accordance with the Periodic Table of the Elements, CAS version, Handbook of Chemistry and Physics, $75^{th}$ Ed. Additionally, general principles of organic chemistry are described in "Organic Chemistry," Thomas Sorrell, University Science Books, Sausalito: 1999, and "March's Advanced Organic Chemistry," $5^{th}$ Ed., Ed.: Smith, M. B. and March, J., John Wiley & Sons, New York: 2001, the entire contents of which are hereby incorporated by reference.

As used herein, the term "compounds of the invention" refers to the compounds of formula I, and all of the embodiments thereof, as described herein.

As used herein, the term "compound," when referring to the compounds of the invention, refers to a collection of molecules having identical chemical structures, except that there may be isotopic variation amongst the constituent atoms of the molecules. The term "compound" includes such a collection of molecules without regard to the purity of a given sample containing the collection of molecules. Thus, the term "compound" includes such a collection of molecules in pure form or in a mixture (e.g., solution, suspension, or colloid) with one or more other substances.

In the specification and claims, unless otherwise specified, any atom not specifically designated as a particular isotope in any compound of the invention is meant to represent any stable isotope of the specified element. In the Examples, where an atom is not specifically designated as a particular isotope in any compound of the invention, no effort was made to enrich that atom in a particular isotope, and therefore a person of ordinary skill in the art would understand that such atom likely was present at approximately the natural abundance isotopic composition of the specified element.

As used herein, the term "stable," when referring to an isotope, means that the isotope is not known to undergo spontaneous radioactive decay. Stable isotopes include, but are not limited to, the isotopes for which no decay mode is identified in V. S. Shirley & C. M. Lederer, Isotopes Project, Nuclear Science Division, Lawrence Berkeley Laboratory, Table of Nuclides (January 1980).

As used herein in the specification and claims, "H" refers to hydrogen and includes any stable isotope of hydrogen. In the Examples, where an atom is designated as "H," no effort was made to enrich that atom in a particular isotope of hydrogen, and therefore a person of ordinary skill in the art would understand that such hydrogen atom likely was present at approximately the natural abundance isotopic composition of hydrogen.

As used herein, "D" and "d" both refer to deuterium ($^2H$).

In some embodiments, the compounds of the invention, and pharmaceutically acceptable salts thereof, include one or more atoms having an atomic mass or mass number which differs from the atomic mass or mass number of the most abundant isotope of the specified element ("isotope-labelled" compounds and salts). Examples of stable isotopes which are commercially available and suitable for the invention include without limitation isotopes of hydrogen, carbon, nitrogen, oxygen, and phosphorus, for example $^2$H, $^{13}$C, $^{15}$N, $^{18}$O, $^{17}$O, and $^{31}$P, respectively.

The isotope-labelled compounds and salts can be used in a number of beneficial ways, including as medicaments. In some embodiments, the isotope-labelled compounds and salts are deuterium ($^2$H)-labelled. Deuterium ($^2$H)-labelled compounds and salts are therapeutically useful with potential therapeutic advantages over the non-$^2$H-labelled compounds. In general, deuterium ($^2$H)-labelled compounds and salts can have higher metabolic stability as compared to those that are not isotope-labelled owing to the kinetic isotope effect described below. Higher metabolic stability translates directly into an increased in vivo half-life or lower dosages, which under most circumstances would represent a preferred embodiment of the present invention. The isotope-labelled compounds and salts can usually be prepared by carrying out the procedures disclosed in the synthesis schemes, the examples and the related description, replacing a non-isotope-labelled reactant by a readily available isotope-labelled reactant.

The deuterium ($^2$H)-labelled compounds and salts can manipulate the rate of oxidative metabolism of the compound by way of the primary kinetic isotope effect. The primary kinetic isotope effect is a change of the rate for a chemical reaction that results from exchange of isotopic nuclei, which in turn is caused by the change in ground state energies of the covalent bonds involved in the reaction. Exchange of a heavier isotope usually results in a lowering of the ground state energy for a chemical bond and thus causes a reduction in the rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_H/k_D$=2-7 are typical. For a further discussion, see S. L. Harbeson and R. D. Tung, *Deuterium In Drug Discovery and Development*, Ann. Rep. Med. Chem. 2011, 46, 403-417, incorporated in its entirety herein by reference.

The concentration of an isotope (e.g., deuterium) incorporated at a given position of an isotope-labelled compound of the invention, or a pharmaceutically acceptable salt thereof, may be defined by the isotopic enrichment factor. The term "isotopic enrichment factor," as used herein, means the ratio between the abundance of an isotope at a given position in an isotope-labeled compound (or salt) and the natural abundance of the isotope.

Where an atom in a compound of the invention, or a pharmaceutically acceptable salt thereof, is designated as deuterium, such compound (or salt) has an isotopic enrichment factor for such atom of at least 3000 (45% deuterium incorporation). In some embodiments, the isotopic enrichment factor is at least 3500 (52.5% deuterium incorporation), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333 (95% deuterium incorporation), at least 6466.7 (97% deuterium incorporation), at least 6600 (99% deuterium incorporation), or at least 6633.3 (99.5% deuterium incorporation).

In some embodiments, the positions not designated specifically as "D," "d," or "deuterium" in the compounds of the invention shall be understood to have hydrogen at its natural abundance isotopic composition.

Salts, Compositions, Uses, Formulation, Administration and Additional Agents
Pharmaceutically Acceptable Salts and Compositions As discussed herein, the invention provides compounds, and pharmaceutically acceptable salts thereof, that are inhibitors of voltage-gated sodium channels, and thus the present compounds, and pharmaceutically acceptable salts thereof, are useful for the treatment of diseases, disorders, and conditions including, but not limited to chronic pain, gut pain, neuropathic pain, musculoskeletal pain, acute pain, inflammatory pain, cancer pain, idiopathic pain, postsurgical pain (e.g., bunionectomy pain or abdominoplasty pain), visceral pain, multiple sclerosis, Charcot-Marie-Tooth syndrome, incontinence, pathological cough, or cardiac arrhythmia. Accordingly, in another aspect of the invention, pharmaceutical compositions are provided, wherein these compositions comprise a compound as described herein, or a pharmaceutically acceptable salt thereof, and optionally comprise a pharmaceutically acceptable carrier, adjuvant or vehicle. In certain embodiments, these compositions optionally further comprise one or more additional therapeutic agents. In some embodiments, the additional therapeutic agent is a sodium channel inhibitor.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" of a compound of this invention includes any non-toxic salt that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of a voltage-gated sodium channel.

Pharmaceutically acceptable salts are well known in the art. For example, S. M. Berge, et al. describe pharmaceutically acceptable salts in detail in *J. Pharmaceutical Sciences*, 1977, 66, 1-19, incorporated herein by reference. Pharmaceutically acceptable salts of the compound of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

In some embodiments, a pharmaceutically acceptable salt of

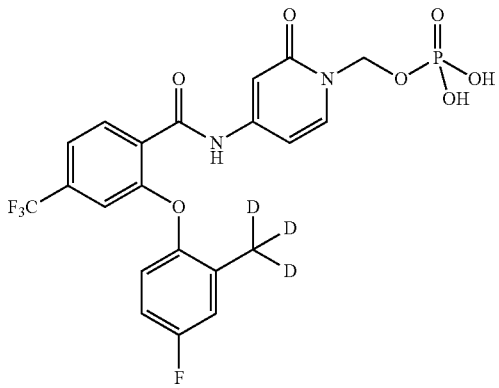 [SMILES: [2H]C([2H])([2H])c1cc(F)ccc1Oc1cc(C(F)(F)F)ccc1C(=O)Nc1ccn(COP(=O)(O)O)c(=O)c1]

has the formula:

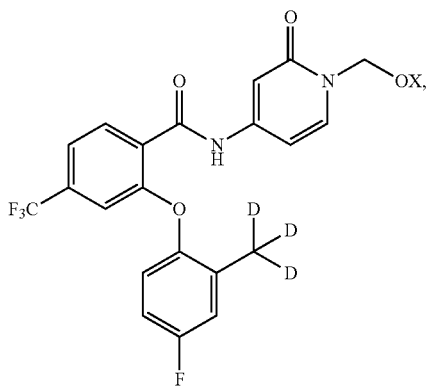

wherein X is —PO(OH)O$^-$M$^+$, —PO(O$^-$)$_2$.2M$^+$, or —PO(O$^-$)$_2$.D$^{2+}$; M$^+$ is a pharmaceutically acceptable monovalent cation; and D$^{2+}$ is a pharmaceutically acceptable divalent cation.

As used herein, the term "monovalent cation" (M$^+$) refers to a cation bearing a single unit of positive charge. Monovalent cations include ammonium (e.g., N(R$^9$)$_4$, wherein R$^9$ is H or C$_1$-C$_4$ alkyl), alkali metal ions such as sodium, lithium and potassium ions, dicyclohexylamine ion, and N-methyl-D-glucamine ion. It is recognized that if the definition 2M$^+$ is present, each of M$^+$ may be the same or different.

As used herein, the term "divalent cation" (D$^{2+}$) refers to a cation bearing two units of positive charge. Divalent cations include alkaline earth metal ions such as calcium and magnesium ions, as well as divalent aluminum ions.

The terms "monovalent cation" and "divalent cation" include amino acid cations such as monovalent or divalent ions of arginine, lysine, ornithine, and so forth. The basic nitrogen-containing groups may be protonated or may be quaternized with such agents as: lower alkyl halides, such as methyl, ethyl, propyl, and butyl chloride, bromides and iodides; dialkyl sulfates like dimethyl, diethyl, dibutyl; diamyl sulfates; long chain halides such as decyl, lauryl, myristyl and stearyl chlorides, bromides and iodides; aralkyl halides like benzyl bromide and others.

As described herein, the pharmaceutically acceptable compositions of the invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

In another aspect, the invention features a pharmaceutical composition comprising a compound of the invention, or a pharmaceutically acceptable salt thereof, and a pharmaceutically acceptable carrier.

In another aspect, the invention features a pharmaceutical composition comprising a therapeutically effective amount of a compound, or a pharmaceutically acceptable salt thereof, and one or more pharmaceutically acceptable carriers or vehicles.

Uses of Compounds and Pharmaceutically Acceptable Salts and Compositions

In another aspect, the invention features a method of inhibiting a voltage-gated sodium channel in a subject comprising administering to the subject a compound of the invention or a pharmaceutically acceptable salt thereof or a pharmaceutical composition thereof. In another aspect, the voltage-gated sodium channel is Nav1.8.

In yet another aspect, the invention features a method of treating or lessening the severity in a subject of chronic pain, gut pain, neuropathic pain, musculoskeletal pain, acute pain, inflammatory pain, cancer pain, idiopathic pain, postsurgical pain (e.g., bunionectomy pain or abdominoplasty pain), visceral pain, multiple sclerosis, Charcot-Marie-Tooth syndrome, incontinence, pathological cough, or cardiac arrhythmia comprising administering an effective amount of a compound of the invention, a pharmaceutically acceptable salt thereof or a pharmaceutical composition thereof.

In yet another aspect, the invention features a method of treating or lessening the severity in a subject of chronic pain, gut pain, neuropathic pain, musculoskeletal pain, acute pain, inflammatory pain, cancer pain, idiopathic pain, postsurgical pain, bunionectomy pain, multiple sclerosis, Charcot-Marie-Tooth syndrome, incontinence, or cardiac arrhythmia comprising administering an effective amount of a compound of the invention, a pharmaceutically acceptable salt thereof or a pharmaceutical composition thereof.

In yet another aspect, the invention features a method of treating or lessening the severity in a subject of gut pain, wherein gut pain comprises inflammatory bowel disease pain, Crohn's disease pain or interstitial cystitis pain wherein said method comprises administering an effective amount of a compound of the invention, a pharmaceutically acceptable salt thereof or a pharmaceutical composition thereof.

In yet another aspect, the invention features a method of treating or lessening the severity in a subject of neuropathic pain comprising administering an effective amount of a compound of the invention, a pharmaceutically acceptable salt thereof or a pharmaceutical composition thereof. In some aspects, the neuropathic pain comprises post-herpetic neuralgia or idiopathic small-fiber neuropathy. As used herein, the phrase "idiopathic small-fiber neuropathy" shall be understood to include any small fiber neuropathy.

In yet another aspect, the invention features a method of treating or lessening the severity in a subject of neuropathic pain, wherein neuropathic pain comprises post-herpetic neuralgia, diabetic neuralgia, painful HIV-associated sensory neuropathy, trigeminal neuralgia, burning mouth syndrome, post-amputation pain, phantom pain, painful neuroma; traumatic neuroma; Morton's neuroma; nerve entrapment injury, spinal stenosis, carpal tunnel syndrome, radicular pain, sciatica pain; nerve avulsion injury, brachial plexus avulsion injury; complex regional pain syndrome, drug therapy induced neuralgia, cancer chemotherapy induced neuralgia, anti-retroviral therapy induced neuralgia; post spinal cord injury pain, idiopathic small-fiber neuropathy, idiopathic sensory neuropathy or trigeminal autonomic cephalalgia wherein said method comprises administering an effective amount of a compound of the invention, a pharmaceutically acceptable salt thereof or a pharmaceutical composition thereof.

In yet another aspect, the invention features a method of treating or lessening the severity in a subject of musculoskeletal pain comprising administering an effective amount of a compound of the invention, a pharmaceutically acceptable salt thereof or a pharmaceutical composition thereof. In some aspects, the musculoskeletal pain comprises osteoarthritis pain.

In yet another aspect, the invention features a method of treating or lessening the severity in a subject of musculoskeletal pain, wherein musculoskeletal pain comprises osteoarthritis pain, back pain, cold pain, burn pain or dental pain wherein said method comprises administering an effective amount of a compound of the invention, a pharmaceutically acceptable salt thereof or a pharmaceutical composition thereof.

In yet another aspect, the invention features a method of treating or lessening the severity in a subject of inflammatory pain, wherein inflammatory pain comprises rheumatoid arthritis pain or vulvodynia wherein said method comprises administering an effective amount of a compound of the invention, a pharmaceutically acceptable salt thereof or a pharmaceutical composition thereof.

In yet another aspect, the invention features a method of treating or lessening the severity in a subject of inflammatory pain, wherein inflammatory pain comprises rheumatoid arthritis pain wherein said method comprises administering an effective amount of a compound of the invention, a pharmaceutically acceptable salt thereof or a pharmaceutical composition thereof.

In yet another aspect, the invention features a method of treating or lessening the severity in a subject of idiopathic pain, wherein idiopathic pain comprises fibromyalgia pain wherein said method comprises administering an effective amount of a compound of the invention, a pharmaceutically acceptable salt thereof or a pharmaceutical composition thereof.

In yet another aspect, the invention features a method of treating or lessening the severity in a subject of pathological cough wherein said method comprises administering an effective amount of a compound of the invention, a pharmaceutically acceptable salt thereof or a pharmaceutical composition thereof.

In yet another aspect, the invention features a method of treating or lessening the severity in a subject of acute pain comprising administering an effective amount of a compound of the invention, a pharmaceutically acceptable salt thereof or a pharmaceutical composition thereof. In some aspects, the acute pain comprises acute post-operative pain.

In yet another aspect, the invention features a method of treating or lessening the severity in a subject of postsurgical pain (e.g., bunionectomy pain or abdominoplasty pain) comprising administering an effective amount of a compound of the invention, a pharmaceutically acceptable salt thereof or a pharmaceutical composition thereof.

In yet another aspect, the invention features a method of treating or lessening the severity in a subject of bunionectomy pain comprising administering an effective amount of a compound of the invention, a pharmaceutically acceptable salt thereof or a pharmaceutical composition thereof.

In yet another aspect, the invention features a method of treating or lessening the severity in a subject of abdominoplasty pain comprising administering an effective amount of a compound of the invention, a pharmaceutically acceptable salt thereof or a pharmaceutical composition thereof.

In yet another aspect, the invention features a method of treating or lessening the severity in a subject of visceral pain comprising administering an effective amount of a compound of the invention, a pharmaceutically acceptable salt thereof or a pharmaceutical composition thereof. In some aspects, the visceral pain comprises visceral pain from abdominoplasty.

In yet another aspect, the invention features a method wherein the subject is treated with one or more additional therapeutic agents administered concurrently with, prior to, or subsequent to treatment with an effective amount of the compound, pharmaceutically acceptable salt or pharmaceutical composition. In some embodiments, the additional therapeutic agent is a sodium channel inhibitor.

In another aspect, the invention features a method of inhibiting a voltage-gated sodium channel in a biological sample comprising contacting the biological sample with an effective amount of a compound of the invention, a pharmaceutically acceptable salt thereof or a pharmaceutical composition thereof. In another aspect, the voltage-gated sodium channel is Nav1.8.

In another aspect, the invention features a method of treating or lessening the severity in a subject of acute pain, chronic pain, neuropathic pain, inflammatory pain, arthritis, migraine, cluster headaches, trigeminal neuralgia, herpetic neuralgia, general neuralgias, epilepsy, epilepsy conditions, neurodegenerative disorders, psychiatric disorders, anxiety, depression, bipolar disorder, myotonia, arrhythmia, movement disorders, neuroendocrine disorders, ataxia, multiple sclerosis, irritable bowel syndrome, incontinence, pathological cough, visceral pain, osteoarthritis pain, postherpetic neuralgia, diabetic neuropathy, radicular pain, sciatica, back pain, head pain, neck pain, severe pain, intractable pain, nociceptive pain, breakthrough pain, postsurgical pain (e.g., bunionectomy pain or abdominoplasty pain), cancer pain, stroke, cerebral ischemia, traumatic brain injury, amyotrophic lateral sclerosis, stress induced angina, exercise induced angina, palpitations, hypertension, or abnormal gastro-intestinal motility, comprising administering an effective amount of a compound of the invention, a pharmaceutically acceptable salt thereof or a pharmaceutical composition thereof.

In another aspect, the invention features a method of treating or lessening the severity in a subject of femur cancer pain; non-malignant chronic bone pain; rheumatoid arthritis; osteoarthritis; spinal stenosis; neuropathic low back pain; myofascial pain syndrome; fibromyalgia; temporomandibular joint pain; chronic visceral pain, abdominal pain; pancreatic pain; IBS pain; chronic and acute headache pain; migraine; tension headache; cluster headaches; chronic and acute neuropathic pain, post-herpetic neuralgia; diabetic neuropathy; HIV-associated neuropathy; trigeminal neuralgia; Charcot-Marie-Tooth neuropathy; hereditary sensory neuropathy; peripheral nerve injury; painful neuromas; ectopic proximal and distal discharges; radiculopathy; chemotherapy induced neuropathic pain; radiotherapy-induced neuropathic pain; post-mastectomy pain; central pain; spinal cord injury pain; post-stroke pain; thalamic pain; complex regional pain syndrome; phantom pain; intractable pain; acute pain, acute post-operative pain; acute musculoskeletal pain; joint pain; mechanical low back pain; neck pain; tendonitis; injury pain; exercise pain; acute visceral pain; pyelonephritis; appendicitis; cholecystitis; intestinal obstruction; hernias; chest pain, cardiac pain; pelvic pain, renal colic pain, acute obstetric pain, labor pain; cesarean section pain; acute inflammatory pain, burn pain, trauma pain; acute intermittent pain, endometriosis; acute herpes zoster pain; sickle cell anemia; acute pancreatitis; breakthrough pain; orofacial pain; sinusitis pain; dental pain; multiple sclerosis (MS) pain; pain in depression; leprosy pain; Behcet's disease pain; adiposis dolorosa; phlebitic pain; Guillain-Barre pain; painful legs and moving toes; Haglund syndrome; erythromelalgia pain; Fabry's disease pain; bladder and urogenital disease; urinary incontinence, pathological cough; hyperactive bladder; painful bladder syndrome; interstitial cystitis (IC); prostatitis; complex regional pain syndrome (CRPS), type I, complex regional pain syndrome (CRPS) type II; widespread pain, paroxysmal extreme pain, pruritus, tinnitus, or angina-induced pain, comprising administering an effective amount of a compound of the invention, a pharmaceutically acceptable salt thereof or a pharmaceutical composition thereof.

Compounds, Pharmaceutically Acceptable Salts, and Compositions for Use

In another aspect, the invention features a compound of the invention, or a pharmaceutically acceptable salt or pharmaceutical composition thereof, for use as a medicament.

In another aspect, the invention features a compound of the invention, or a pharmaceutically acceptable salt or pharmaceutical composition thereof, for use in a method of inhibiting a voltage-gated sodium channel in a subject. In another aspect, the voltage-gated sodium channel is Nav1.8.

In another aspect, the invention features a compound of the invention, or a pharmaceutically acceptable salt or pharmaceutical composition thereof, for use in a method of treating or lessening the severity in a subject of chronic pain, gut pain, neuropathic pain, musculoskeletal pain, acute pain, inflammatory pain, cancer pain, idiopathic pain, postsurgical pain (e.g., bunionectomy pain or abdominoplasty pain), visceral pain, multiple sclerosis, Charcot-Marie-Tooth syndrome, incontinence, pathological cough, or cardiac arrhythmia.

In another aspect, the invention features a compound of the invention, or a pharmaceutically acceptable salt or pharmaceutical composition thereof, for use in a method of treating or lessening the severity in a subject of chronic pain, gut pain, neuropathic pain, musculoskeletal pain, acute pain, inflammatory pain, cancer pain, idiopathic pain, postsurgical pain, bunionectomy pain, multiple sclerosis, Charcot-Marie-Tooth syndrome, incontinence, or cardiac arrhythmia.

In another aspect, the invention features a compound of the invention, or a pharmaceutically acceptable salt or pharmaceutical composition thereof, for use in a method of treating or lessening the severity in a subject of gut pain, wherein gut pain comprises inflammatory bowel disease pain, Crohn's disease pain or interstitial cystitis pain.

In another aspect, the invention features a compound of the invention, or a pharmaceutically acceptable salt or pharmaceutical composition thereof, for use in a method of treating or lessening the severity in a subject of neuropathic pain. In some aspects, the neuropathic pain comprises post-herpetic neuralgia or idiopathic small-fiber neuropathy. As used herein, the phrase "idiopathic small-fiber neuropathy" shall be understood to include any small fiber neuropathy.

In another aspect, the invention features a compound of the invention, or a pharmaceutically acceptable salt or pharmaceutical composition thereof, for use in a method of treating or lessening the severity in a subject of neuropathic pain, wherein neuropathic pain comprises post-herpetic neuralgia, diabetic neuralgia, painful HIV-associated sensory neuropathy, trigeminal neuralgia, burning mouth syndrome, post-amputation pain, phantom pain, painful neuroma; traumatic neuroma; Morton's neuroma; nerve entrapment injury, spinal stenosis, carpal tunnel syndrome, radicular pain, sciatica pain; nerve avulsion injury, brachial plexus avulsion injury; complex regional pain syndrome, drug therapy induced neuralgia, cancer chemotherapy induced neuralgia, anti-retroviral therapy induced neuralgia; post spinal cord injury pain, idiopathic small-fiber neuropathy, idiopathic sensory neuropathy or trigeminal autonomic cephalalgia.

In another aspect, the invention features a compound of the invention, or a pharmaceutically acceptable salt or pharmaceutical composition thereof, for use in a method of treating or lessening the severity in a subject of musculoskeletal pain. In some aspects, the musculoskeletal pain comprises osteoarthritis pain.

In another aspect, the invention features a compound of the invention, or a pharmaceutically acceptable salt or pharmaceutical composition thereof, for use in a method of treating or lessening the severity in a subject of musculoskeletal pain, wherein musculoskeletal pain comprises osteoarthritis pain, back pain, cold pain, burn pain or dental pain.

In another aspect, the invention features a compound of the invention, or a pharmaceutically acceptable salt or pharmaceutical composition thereof, for use in a method of treating or lessening the severity in a subject of inflammatory pain, wherein inflammatory pain comprises rheumatoid arthritis pain or vulvodynia.

In another aspect, the invention features a compound of the invention, or a pharmaceutically acceptable salt or pharmaceutical composition thereof, for use in a method of treating or lessening the severity in a subject of inflammatory pain, wherein inflammatory pain comprises rheumatoid arthritis pain.

In another aspect, the invention features a compound of the invention, or a pharmaceutically acceptable salt or pharmaceutical composition thereof, for use in a method of treating or lessening the severity in a subject of idiopathic pain, wherein idiopathic pain comprises fibromyalgia pain.

In another aspect, the invention features a compound of the invention, or a pharmaceutically acceptable salt or pharmaceutical composition thereof, for use in a method of treating or lessening the severity in a subject of pathological cough.

In another aspect, the invention features a compound of the invention, or a pharmaceutically acceptable salt or pharmaceutical composition thereof, for use in a method of treating or lessening the severity in a subject of acute pain. In some aspects, the acute pain comprises acute post-operative pain.

In another aspect, the invention features a compound of the invention, or a pharmaceutically acceptable salt or pharmaceutical composition thereof, for use in a method of treating or lessening the severity in a subject of postsurgical pain (e.g., bunionectomy pain or abdominoplasty pain).

In another aspect, the invention features a compound of the invention, or a pharmaceutically acceptable salt or pharmaceutical composition thereof, for use in a method of treating or lessening the severity in a subject of bunionectomy pain.

In another aspect, the invention features a compound of the invention, or a pharmaceutically acceptable salt or pharmaceutical composition thereof, for use in a method of treating or lessening the severity in a subject of abdominoplasty pain.

In another aspect, the invention features a compound of the invention, or a pharmaceutically acceptable salt or pharmaceutical composition thereof, for use in a method of treating or lessening the severity in a subject of visceral pain. In some aspects, the visceral pain comprises visceral pain from abdominoplasty.

In another aspect, the invention features a compound of the invention, or a pharmaceutically acceptable salt or pharmaceutical composition thereof, for use in a method wherein the subject is treated with one or more additional therapeutic agents administered concurrently with, prior to, or subsequent to treatment with an effective amount of the compound, pharmaceutically acceptable salt or pharmaceutical composition. In some embodiments, the additional therapeutic agent is a sodium channel inhibitor.

In another aspect, the invention features a compound of the invention, or a pharmaceutically acceptable salt or pharmaceutical composition thereof, for use in a method of inhibiting a voltage-gated sodium channel in a biological sample comprising contacting the biological sample with an effective amount of a compound of the invention, a pharmaceutically acceptable salt thereof or a pharmaceutical composition thereof. In another aspect, the voltage-gated sodium channel is Nav1.8.

In another aspect, the invention features a compound of the invention, or a pharmaceutically acceptable salt or pharmaceutical composition thereof, for use in a method of treating or lessening the severity in a subject of acute pain, chronic pain, neuropathic pain, inflammatory pain, arthritis, migraine, cluster headaches, trigeminal neuralgia, herpetic neuralgia, general neuralgias, epilepsy, epilepsy conditions, neurodegenerative disorders, psychiatric disorders, anxiety, depression, bipolar disorder, myotonia, arrhythmia, movement disorders, neuroendocrine disorders, ataxia, multiple sclerosis, irritable bowel syndrome, incontinence, pathological cough, visceral pain, osteoarthritis pain, postherpetic neuralgia, diabetic neuropathy, radicular pain, sciatica, back pain, head pain, neck pain, severe pain, intractable pain, nociceptive pain, breakthrough pain, postsurgical pain (e.g., bunionectomy pain or abdominoplasty pain), cancer pain, stroke, cerebral ischemia, traumatic brain injury, amyotrophic lateral sclerosis, stress induced angina, exercise induced angina, palpitations, hypertension, or abnormal gastro-intestinal motility.

In another aspect, the invention features a compound of the invention, or a pharmaceutically acceptable salt or pharmaceutical composition thereof, for use in a method of treating or lessening the severity in a subject of femur cancer pain; non-malignant chronic bone pain; rheumatoid arthritis; osteoarthritis; spinal stenosis; neuropathic low back pain; myofascial pain syndrome; fibromyalgia; temporomandibular joint pain; chronic visceral pain, abdominal pain; pancreatic pain; IBS pain; chronic and acute headache pain; migraine; tension headache; cluster headaches; chronic and acute neuropathic pain, post-herpetic neuralgia; diabetic neuropathy; HIV-associated neuropathy; trigeminal neuralgia; Charcot-Marie-Tooth neuropathy; hereditary sensory neuropathy; peripheral nerve injury; painful neuromas; ectopic proximal and distal discharges; radiculopathy; chemotherapy induced neuropathic pain; radiotherapy-induced neuropathic pain; post-mastectomy pain; central pain; spinal cord injury pain; post-stroke pain; thalamic pain; complex regional pain syndrome; phantom pain; intractable pain; acute pain, acute post-operative pain; acute musculoskeletal pain; joint pain; mechanical low back pain; neck pain; tendonitis; injury pain; exercise pain; acute visceral pain; pyelonephritis; appendicitis; cholecystitis; intestinal obstruction; hernias; chest pain, cardiac pain; pelvic pain, renal colic pain, acute obstetric pain, labor pain; cesarean section pain; acute inflammatory pain, burn pain, trauma pain; acute intermittent pain, endometriosis; acute herpes zoster pain; sickle cell anemia; acute pancreatitis; breakthrough pain; orofacial pain; sinusitis pain; dental pain; multiple sclerosis (MS) pain; pain in depression; leprosy pain; Behcet's disease pain; adiposis dolorosa; phlebitic pain; Guillain-Barre pain; painful legs and moving toes; Haglund syndrome; erythromelalgia pain; Fabry's disease pain; bladder and urogenital disease; urinary incontinence, pathological cough; hyperactive bladder; painful bladder syndrome; interstitial cystitis (IC); prostatitis; complex regional pain syndrome (CRPS), type I, complex regional pain syndrome (CRPS) type II; widespread pain, paroxysmal extreme pain, pruritus, tinnitus, or angina-induced pain.

Manufacture of Medicaments

In another aspect, the invention provides the use of a compound of the invention, or a pharmaceutically acceptable salt or pharmaceutical composition thereof, for the manufacture of a medicament.

In another aspect, the invention provides the use of a compound of the invention, a pharmaceutically acceptable salt thereof, or a pharmaceutical composition thereof for the manufacture of a medicament for use in inhibiting a voltage-gated sodium channel. In another aspect, the voltage-gated sodium channel is $Na_V1.8$.

In yet another aspect, the invention provides the use of a compound of the invention, a pharmaceutically acceptable salt thereof, or a pharmaceutical composition thereof for the manufacture of a medicament for use in treating or lessening the severity in a subject of chronic pain, gut pain, neuropathic pain, musculoskeletal pain, acute pain, inflammatory pain, cancer pain, idiopathic pain, postsurgical pain (e.g., bunionectomy pain or abdominoplasty pain), visceral pain, multiple sclerosis, Charcot-Marie-Tooth syndrome, incontinence, pathological cough, or cardiac arrhythmia.

In yet another aspect, the invention provides the use of a compound of the invention, a pharmaceutically acceptable salt thereof, or a pharmaceutical composition thereof for the manufacture of a medicament for use in treating or lessening the severity in a subject of chronic pain, gut pain, neuropathic pain, musculoskeletal pain, acute pain, inflammatory pain, cancer pain, idiopathic pain, postsurgical pain, bunionectomy pain, multiple sclerosis, Charcot-Marie-Tooth syndrome, incontinence, or cardiac arrhythmia.

In yet another aspect, the invention provides the use of the compound, pharmaceutically acceptable salt, or pharmaceutical composition described herein for the manufacture of a medicament for use in treating or lessening the severity in a subject of gut pain, wherein gut pain comprises inflammatory bowel disease pain, Crohn's disease pain or interstitial cystitis pain.

In yet another aspect, the invention provides a compound of the invention, a pharmaceutically acceptable salt thereof, or a pharmaceutical composition thereof for the manufacture of a medicament for use in treating or lessening the severity in a subject of neuropathic pain. In some aspects, the neuropathic pain comprises post-herpetic neuralgia or idiopathic small-fiber neuropathy.

In yet another aspect, the invention provides the use of a compound of the invention, a pharmaceutically acceptable salt thereof, or a pharmaceutical composition thereof for the manufacture of a medicament for use in a treating or lessening the severity in a subject of neuropathic pain, wherein neuropathic pain comprises post-herpetic neuralgia, diabetic neuralgia, painful HIV-associated sensory neuropathy, trigeminal neuralgia, burning mouth syndrome, post-amputation pain, phantom pain, painful neuroma; traumatic neuroma; Morton's neuroma; nerve entrapment injury, spinal stenosis, carpal tunnel syndrome, radicular pain, sciatica pain; nerve avulsion injury, brachial plexus avulsion injury; complex regional pain syndrome, drug therapy induced neuralgia, cancer chemotherapy induced neuralgia, anti-retroviral therapy induced neuralgia; post spinal cord injury pain, idiopathic small-fiber neuropathy, idiopathic sensory neuropathy or trigeminal autonomic neuropathy.

In yet another aspect, the invention provides the use of a compound of the invention, a pharmaceutically acceptable salt thereof, or a pharmaceutical composition thereof for the manufacture of a medicament for use in treating or lessening the severity in a subject of musculoskeletal pain. In some aspects the musculoskeletal pain comprises osteoarthritis pain.

In yet another aspect, the invention provides the use of a compound of the invention, a pharmaceutically acceptable salt thereof, or a pharmaceutical composition thereof for the manufacture of a medicament for use in treating or lessening the severity in a subject of musculoskeletal pain, wherein musculoskeletal pain comprises osteoarthritis pain, back pain, cold pain, burn pain or dental pain.

In yet another aspect, the invention provides the use of a compound of the invention, a pharmaceutically acceptable salt thereof, or a pharmaceutical composition thereof for the manufacture of a medicament for use in treating or lessening the severity in a subject of inflammatory pain, wherein inflammatory pain comprises rheumatoid arthritis pain or vulvodynia.

In yet another aspect, the invention provides the use of a compound of the invention, a pharmaceutically acceptable salt thereof, or a pharmaceutical composition thereof for the manufacture of a medicament for use in treating or lessening the severity in a subject of inflammatory pain, wherein inflammatory pain comprises rheumatoid arthritis pain.

In yet another aspect, the invention provides the use of a compound of the invention, a pharmaceutically acceptable salt thereof, or a pharmaceutical composition thereof for the manufacture of a medicament for use in treating or lessening the severity in a subject of idiopathic pain, wherein idiopathic pain comprises fibromyalgia pain.

In yet another aspect, the invention provides the use of a compound of the invention, a pharmaceutically acceptable salt thereof, or a pharmaceutical composition thereof for the manufacture of a medicament for use in treating or lessening the severity in a subject of pathological cough.

In yet another aspect, the invention provides the use of a compound of the invention, a pharmaceutically acceptable salt thereof, or a pharmaceutical composition thereof for the manufacture of a medicament for use in treating or lessening the severity in a subject of acute pain. In some aspects, the acute pain comprises acute post-operative pain.

In yet another aspect, the invention provides the use of a compound of the invention, a pharmaceutically acceptable salt thereof, or a pharmaceutical composition thereof for the manufacture of a medicament for use in treating or lessening the severity in a subject of postsurgical pain (e.g., bunionectomy pain or abdominoplasty pain).

In yet another aspect, the invention provides the use of a compound of the invention, a pharmaceutically acceptable salt thereof, or a pharmaceutical composition thereof for the manufacture of a medicament for use in treating or lessening the severity in a subject of bunionectomy pain.

In yet another aspect, the invention provides the use of a compound of the invention, a pharmaceutically acceptable salt thereof, or a pharmaceutical composition thereof for the manufacture of a medicament for use in treating or lessening the severity in a subject of abdominoplasty pain.

In yet another aspect, the invention provides the use of a compound of the invention, a pharmaceutically acceptable salt thereof, or a pharmaceutical composition thereof for the manufacture of a medicament for use in treating or lessening the severity in a subject of visceral pain. In some aspects, the visceral pain comprises visceral pain from abdominoplasty.

In yet another aspect, the invention provides the use of a compound of the invention, a pharmaceutically acceptable salt thereof, or a pharmaceutical composition thereof for the manufacture of a medicament for use in combination with one or more additional therapeutic agents administered concurrently with, prior to, or subsequent to treatment with the compound or pharmaceutical composition. In some embodiments, the additional therapeutic agent is a sodium channel inhibitor.

In another aspect, the invention provides the use of a compound of the invention, a pharmaceutically acceptable salt thereof, or a pharmaceutical composition thereof for the manufacture of a medicament for use in treating or lessening the severity of acute pain, chronic pain, neuropathic pain, inflammatory pain, arthritis, migraine, cluster headaches, trigeminal neuralgia, herpetic neuralgia, general neuralgias, epilepsy, epilepsy conditions, neurodegenerative disorders, psychiatric disorders, anxiety, depression, bipolar disorder, myotonia, arrhythmia, movement disorders, neuroendocrine disorders, ataxia, multiple sclerosis, irritable bowel syndrome, incontinence, pathological cough, visceral pain, osteoarthritis pain, postherpetic neuralgia, diabetic neuropathy, radicular pain, sciatica, back pain, head pain, neck pain, severe pain, intractable pain, nociceptive pain, breakthrough pain, postsurgical pain (e.g., bunionectomy pain or abdominoplasty pain), cancer pain, stroke, cerebral ischemia, traumatic brain injury, amyotrophic lateral sclerosis, stress induced angina, exercise induced angina, palpitations, hypertension, or abnormal gastro-intestinal motility.

In another aspect, the invention provides the use of a compound of the invention, a pharmaceutically acceptable salt thereof, or a pharmaceutical composition thereof for the manufacture of a medicament for use in treating or lessening the severity of femur cancer pain; non-malignant chronic bone pain; rheumatoid arthritis; osteoarthritis; spinal stenosis; neuropathic low back pain; myofascial pain syndrome; fibromyalgia; temporomandibular joint pain; chronic visceral pain, abdominal pain; pancreatic pain; IBS pain; chronic and acute headache pain; migraine; tension headache; cluster headaches; chronic and acute neuropathic pain, post-herpetic neuralgia; diabetic neuropathy; HIV-associated neuropathy; trigeminal neuralgia; Charcot-Marie-Tooth neuropathy; hereditary sensory neuropathy; peripheral nerve injury; painful neuromas; ectopic proximal and distal discharges; radiculopathy; chemotherapy induced neuropathic pain; radiotherapy-induced neuropathic pain; post-mastectomy pain; central pain; spinal cord injury pain; post-stroke pain; thalamic pain; complex regional pain syndrome; phantom pain; intractable pain; acute pain, acute post-operative pain; acute musculoskeletal pain; joint pain; mechanical low back pain; neck pain; tendonitis; injury pain; exercise pain; acute visceral pain; pyelonephritis; appendicitis; cholecystitis; intestinal obstruction; hernias; chest pain, cardiac pain; pelvic pain, renal colic pain, acute obstetric pain, labor pain; cesarean section pain; acute inflammatory, burn pain, trauma pain; acute intermittent pain, endometriosis; acute herpes zoster pain; sickle cell anemia; acute pancreatitis; breakthrough pain; orofacial pain; sinusitis pain; dental pain; multiple sclerosis (MS) pain; pain in depression; leprosy pain; Behcet's disease pain; adiposis dolorosa; phlebitic pain; Guillain-Barre pain; painful legs and moving toes; Haglund syndrome; erythromelalgia pain; Fabry's disease pain; bladder and urogenital disease; urinary incontinence; pathological cough; hyperactive bladder; painful bladder syndrome; interstitial cystitis (IC); prostatitis; complex regional pain syndrome (CRPS) type I; complex regional pain syndrome (CRPS) type II; widespread pain, paroxysmal extreme pain, pruritus, tinnitus, or angina-induced pain. Administration of Pharmaceutically Acceptable Salts and Compositions.

In certain embodiments of the invention an "effective amount" of a compound of the invention, a pharmaceutically acceptable salt thereof, or a pharmaceutical composition thereof is that amount effective for treating or lessening the severity of one or more of the conditions recited above.

The compounds, salts, and compositions, according to the method of the invention, may be administered using any amount and any route of administration effective for treating or lessening the severity of one or more of the pain or non-pain diseases recited herein. The exact amount required will vary from subject to subject, depending on the species, age, and general condition of the subject, the severity of the condition, the particular agent, its mode of administration, and the like. The compounds, salts, and compositions of the invention are preferably formulated in dosage unit form for ease of administration and uniformity of dosage. The expression "dosage unit form" as used herein refers to a physically discrete unit of agent appropriate for the subject to be treated. It will be understood, however, that the total daily usage of the compounds, salts, and compositions of the invention will be decided by the attending physician within the scope of sound medical judgment. The specific effective dose level for any particular subject or organism will depend upon a variety of factors including the disorder being treated and the severity of the disorder; the activity of the specific compound or salt employed; the specific composition employed; the age, body weight, general health, sex and diet of the subject; the time of administration, route of administration, and rate of excretion of the specific compound or salt employed; the duration of the treatment; drugs used in combination or coincidental with the specific compound or salt employed, and like factors well known in the medical arts. The term "subject" or "patient," as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the condition being treated. In certain embodiments, the compound, salts, and compositions of the invention may be administered orally or parenterally at dosage levels of about 0.001 mg/kg to about 100 mg/kg, or about 0.01 mg/kg to about 50 mg/kg, of subject body weight per day, one or more times a day, effective to obtain the desired therapeutic effect.

Liquid dosage forms for oral administration include, but are not limited to, pharmaceutically acceptable emulsions, microemulsions, solutions, suspensions, syrups and elixirs. In addition to the active compound or salt, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of the compounds of the invention, it is often desirable to slow the absorption of the compounds from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compound or salt of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound or salt is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compound or salt can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound or salt may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound or salt of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as inhibitors of voltage-gated sodium channels. In one embodiment, the compounds are inhibitors of $Na_V1.8$ and thus, without wishing to be bound by any particular theory, the compounds, salts, and compositions are particularly useful for treating or lessening the severity of a disease, condition, or disorder where activation or hyperactivity of $Na_V1.8$ is implicated in the disease, condition, or disorder. When activation or hyperactivity of $Na_V1.8$ is implicated in a particular disease, condition, or disorder, the disease, condition, or disorder may also be referred to as a "$Na_V1.8$-mediated disease, condition or disorder." Accordingly, in another aspect, the invention provides a method for treating or lessening the severity of a disease, condition, or disorder where activation or hyperactivity of $Na_V1.8$ is implicated in the disease state.

The activity of a compound utilized in this invention as an inhibitor of $Na_V1.8$ may be assayed according to methods described generally in International Publication No. WO 2014/120808 A9 and U.S. Publication No. 2014/0213616

A1, both of which are incorporated by reference in their entirety, methods described herein, and other methods known and available to one of ordinary skill in the art.

Additional Therapeutic Agents

It will also be appreciated that the compounds, salts, and pharmaceutically acceptable compositions of the invention can be employed in combination therapies, that is, the compounds, salts, and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated." For example, exemplary additional therapeutic agents include, but are not limited to: nonopioid analgesics (indoles such as Etodolac, Indomethacin, Sulindac, Tolmetin; naphthylalkanones such as Nabumetone; oxicams such as Piroxicam; para-aminophenol derivatives, such as Acetaminophen; propionic acids such as Fenoprofen, Flurbiprofen, Ibuprofen, Ketoprofen, Naproxen, Naproxen sodium, Oxaprozin; salicylates such as Aspirin, Choline magnesium trisalicylate, Diflunisal; fenamates such as meclofenamic acid, Mefenamic acid; and pyrazoles such as Phenylbutazone); or opioid (narcotic) agonists (such as Codeine, Fentanyl, Hydromorphone, Levorphanol, Meperidine, Methadone, Morphine, Oxycodone, Oxymorphone, Propoxyphene, Buprenorphine, Butorphanol, Dezocine, Nalbuphine, and Pentazocine). Additionally, nondrug analgesic approaches may be utilized in conjunction with administration of one or more compounds of the invention. For example, anesthesiologic (intraspinal infusion, neural blockade), neurosurgical (neurolysis of CNS pathways), neurostimulatory (transcutaneous electrical nerve stimulation, dorsal column stimulation), physiatric (physical therapy, orthotic devices, diathermy), or psychologic (cognitive methods-hypnosis, biofeedback, or behavioral methods) approaches may also be utilized Additional appropriate therapeutic agents or approaches are described generally in The Merck Manual, Nineteenth Edition, Ed. Robert S. Porter and Justin L. Kaplan, Merck Sharp & Dohme Corp., a subsidiary of Merck & Co., Inc., 2011, and the Food and Drug Administration website, www.fda.gov, the entire contents of which are hereby incorporated by reference.

In another embodiment, additional appropriate therapeutic agents are selected from the following:

(1) an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;

(2) a nonsteroidal antiinflammatory drug (NSAID), e.g. aspirin, diclofenac, diflunisal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;

(3) a barbiturate sedative, e.g. amobarbital, aprobarbital, butabarbital, butalbital, mephobarbital, metharbital, methohexital, pentobarbital, phenobarbital, secobarbital, talbutal, thiamylal or thiopental;

(4) a benzodiazepine having a sedative action, e.g. chlordiazepoxide, clorazepate, diazepam, flurazepam, lorazepam, oxazepam, temazepam or triazolam;

(5) a histamine ($H_1$) antagonist having a sedative action, e.g. diphenhydramine, pyrilamine, promethazine, chlorpheniramine or chlorcyclizine;

(6) a sedative such as glutethimide, meprobamate, methaqualone or dichloralphenazone;

(7) a skeletal muscle relaxant, e.g. baclofen, carisoprodol, chlorzoxazone, cyclobenzaprine, methocarbamol or orphenadrine;

(8) an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex®), a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2(1H)-quinolinone;

(9) an alpha-adrenergic, e.g. doxazosin, tamsulosin, clonidine, guanfacine, dexmedetomidine, modafinil, or 4-amino-6,7-dimethoxy-2-(5-methane-sulfonamido-1, 2,3,4-tetrahydroisoquinolin-2-yl)-5-(2-pyridyl) quinazoline;

(10) a tricyclic antidepressant, e.g. desipramine, imipramine, amitriptyline or nortriptyline;

(11) an anticonvulsant, e.g. carbamazepine (Tegretol®), lamotrigine, topiramate, lacosamide (Vimpat®) or valproate;

(12) a tachykinin (NK) antagonist, particularly an NK-3, NK-2 or NK-1 antagonist, e.g. (alphaR,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);

(13) a muscarinic antagonist, e.g oxybutynin, tolterodine, propiverine, tropsium chloride, darifenacin, solifenacin, temiverine and ipratropium;

(14) a COX-2 selective inhibitor, e.g. celecoxib, rofecoxib, parecoxib, valdecoxib, deracoxib, etoricoxib, or lumiracoxib;

(15) a coal-tar analgesic, in particular paracetamol;

(16) a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion® or sarizotan;

(17) a vanilloid receptor agonist (e.g. resinferatoxin or civamide) or antagonist (e.g. capsazepine, GRC-15300);

(18) a beta-adrenergic such as propranolol;

(19) a local anaesthetic such as mexiletine;

(20) a corticosteroid such as dexamethasone;

(21) a 5-HT receptor agonist or antagonist, particularly a 5-HT$_{1B/1D}$ agonist such as eletriptan, sumatriptan, naratriptan, zolmitriptan or rizatriptan;

(22) a 5-HT$_{2A}$ receptor antagonist such as R(+)-alpha-(2,3-dimethoxy-phenyl)-1-[2-(4-fluorophenylethyl)]-4-piperidinemethanol (MDL-100907);

(23) a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;

(24) Tramadol®, Tramadol ER (Ultram ER®), Tapentadol ER (Nucynta®);

(25) a PDE5 inhibitor, such as 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)-pyrazino[2',1':6,1]-pyrido[3,4-b]indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pymzolo[4,3-d]pyrimidin-7-one, 4-[(3-chloro-4-methoxybenzyl)amino]-2-[(2S)-2-(hydroxymethyl) pyrrolidin-1-yl]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

(26) an alpha-2-delta ligand such as gabapentin (Neurontin®), gabapentin GR (Gralise®), gabapentin, enacarbil (Horizant®), pregabalin (Lyrica®), 3-methyl gabapentin, (1[alpha],3 [alpha],5 [alpha])(3-amino-methyl-bicyclo [3.2.0]hept-3-yl)-acetic acid, (3 S,5R)-3-aminomethyl-5-methyl-heptanoic acid, (3 S,5R)-3-amino-5-methyl-heptanoic acid, (3 S,5R)-3-amino-5-methyl-octanoic acid, (2S, 4S)-4-(3-chlorophenoxy)proline, (2S,4S)-4-(3-fluorobenzyl)-proline, [(1R,5R,6S)-6-(aminomethyl)bicyclo [3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3 S,5R)-3-aminomethyl-5-methyl-octanoic acid, (3 S,5R)-3-amino-5-methyl-nonanoic acid, (3S,5R)-3-amino-5-methyl-octanoic acid, (3R,4R,5R)-3-amino-4,5-dimethyl-heptanoic acid and (3R,4R,5R)-3-amino-4,5-dimethyl-octanoic acid;

(27) a cannabinoid such as KHK-6188;

(28) metabotropic glutamate subtype 1 receptor (mGluR1) antagonist;

(29) a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,1-fenfluramine, femoxetine, ifoxetine, cyanodothiepin, litoxetine, dapoxetine, nefazodone, cericlamine and trazodone;

(30) a noradrenaline (norepinephrine) reuptake inhibitor, such as maprotiline, lofepramine, mirtazepine, oxaprotiline, fezolamine, tomoxetine, mianserin, bupropion, bupropion metabolite hydroxybupropion, nomifensine and viloxazine (Vivalan®), especially a selective noradrenaline reuptake inhibitor such as reboxetine, in particular (S,S)-reboxetine;

(31) a dual serotonin-noradrenaline reuptake inhibitor, such as venlafaxine, venlafaxine metabolite O-desmethyl-venlafaxine, clomipramine, clomipramine metabolite desmethylclomipramine, duloxetine (Cymbalta®), milnacipran and imipramine;

(32) an inducible nitric oxide synthase (iNOS) inhibitor such as S-[2-[(1-iminoethyl)amino]ethyl]-L-homocysteine, S-[2[(1-iminoethyl)-amino]ethyl]-4,4-dioxo-L-cysteine, S-[2-[(1-iminoethyl)amino]ethyl]-2-methyl-L-cysteine, (2S, 5Z)-2-amino-2-methyl-7-[(1-iminoethyl)amino]-5-heptenoic acid, 2-[[(1R,3S)-3-amino-4-hydroxy-1-(5-thiazolyl)-butyl]thio]-S-chloro-S-pyridinecarbonitrile; 2-[[(1R,3S)-3-amino-4-hydroxy-1-(5-thiazolyl)butyl]thio]-4-chlorobenzonitrile, (2S,4R)-2-amino-4-[[2-chloro-5-(trifluoromethyl)phenyl]thio]-5-thiazolebutanol, 2-[[(1R, 3S)-3-amino-4-hydroxy-1-(5-thiazolyl) butyl]thio]-6-(trifluoromethyl)-3-pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino)ethyl]phenyl]thiophene-2-carboxamidine, NXN-462, or guanidinoethyldisulfide;

(33) an acetylcholinesterase inhibitor such as donepezil;

(34) a prostaglandin E2 subtype 4 (EP4) antagonist such as N-[({2-[4-(2-ethyl-4,6-dimethyl-1H-imidazo[4,5-c]pyridin-1-yl)phenyl]ethyl}amino)-carbonyl]-4-methylbenzenesulfonamide or 4-[(15)-1-({[5-chloro-2-(3-fluorophenoxy) pyridin-3-yl]carbonyl}amino)ethyl]benzoic acid;

(35) a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870;

(36) a 5-lipoxygenase inhibitor, such as zileuton, 6-[(3-fluoro-5-[4-methoxy-3,4,5,6-tetrahydro-2H-pyran-4-yl]) phenoxy-methyl]-1-methyl-2-quinolone (ZD-2138), or 2,3,5-trimethyl-6-(3-pyridylmethyl)-1,4-benzoquinone (CV-6504);

(37) a sodium channel blocker, such as lidocaine, lidocaine plus tetracaine cream (ZRS-201) or eslicarbazepine acetate;

(38) an Na$_V$1.7 blocker, such as XEN-402, XEN403, TV-45070, PF-05089771, CNV1014802, GDC-0276, RG7893 and such as those disclosed in WO2011/140425 (US2011/306607); WO2012/106499 (US2012196869); WO2012/112743 (US2012245136); WO2012/125613 (US2012264749), WO2012/116440 (US2014187533), WO2011026240 (US2012220605), U.S. Pat. Nos. 8,883, 840, 8,466,188, or WO2013/109521 (US2015005304), the entire contents of each application hereby incorporated by reference.

(38a) an Na$_V$1.7 blocker such as (2-benzylspiro[3,4-dihydropyrrolo[1,2-a]pyrazine-1,4'-piperidine]-1'-yl)-(4-isopropoxy-3-methyl-phenyl)methanone, 2,2,2-trifluoro-1-[1'-[3-methoxy-4-[2-(trifluoromethoxy)ethoxy]benzoyl]-2,4-dimethyl-spiro[3,4-dihydropyrrolo[1,2-a]pyrazine-1,4'-piperidine]-6-yl]ethanone, [8-fluoro-2-methyl-6-(trifluoromethyl)spiro[3,4-dihydropyrrolo[1,2-a]pyrazine-1,4'-piperidine]-1'-yl]-(4-isobutoxy-3-methoxy-phenyl) methanone, 1-(4-benzhydrylpiperazin-1-yl)-3-[2-(3,4-dimethylphenoxy)ethoxy]propan-2-ol, (4-butoxy-3-methoxy-phenyl)-[2-methyl-6-(trifluoromethyl)spiro[3,4-dihydropyrrolo[1,2-a]pyrazine-1,4'-piperidine]-1'-yl] methanone, [8-fluoro-2-methyl-6-(trifluoromethyl)spiro[3,4-dihydropyrrolo[1,2-a]pyrazine-1,4'-piperidine]-1'-yl]-(5-isopropoxy-6-methyl-2-pyridyl)methanone, (4-isopropoxy-3-methyl-phenyl)-[2-methyl-6-(1,1,2,2,2-pentafluoroethyl) spiro[3,4-dihydropyrrolo[1,2-a]pyrazine-1,4'-piperidine]-1'-yl]methanone, 5-[2-methyl-4-[2-methyl-6-(2,2,2-trifluoroacetyl)spiro[3,4-dihydropyrrolo[1,2-a]pyrazine-1, 4'-piperidine]-1'-carbonyl]phenyl]pyridine-2-carbonitrile, (4-isopropoxy-3-methyl-phenyl)-[6-(trifluoromethyl)spiro [3,4-dihydro-2H-pyrrolo[1,2-a]pyrazine-1,4'-piperidine]-1'-yl]methanone, 2,2,2-trifluoro-1-[1'-[3-methoxy-4-[2-(trifluoromethoxy)ethoxy]benzoyl]-2-methyl-spiro[3,4-dihydropyrrolo[1,2-a]pyrazine-1,4'-piperidine]-6-yl] ethanone, 2,2,2-trifluoro-1-[1'-(5-isopropoxy-6-methyl-pyridine-2-carbonyl)-3,3-dimethyl-spiro[2,4-dihydropyrrolo[1,2-a]pyrazine-1,4'-piperidine]-6-yl] ethanone, 2,2,2-trifluoro-1-[1'-(5-isopentyloxypyridine-2-carbonyl)-2-methyl-spiro[3,4-dihydropyrrolo[1,2-a] pyrazine-1,4'-piperidine]-6-yl]ethanone, (4-isopropoxy-3-methoxy-phenyl)-[2-methyl-6-(trifluoromethyl)spiro[3,4-dihydropyrrolo[1,2-a]pyrazine-1,4'-piperidine]-1'-yl] methanone, 2,2,2-trifluoro-1-[1'-(5-isopentyloxypyridine-2-carbonyl)-2,4-dimethyl-spiro[3,4-dihydropyrrolo[1,2-a] pyrazine-1,4'-piperidine]-6-yl]ethanone, 1-[(3S)-2,3-dimethyl-1'-[4-(3,3,3-trifluoropropoxymethy)benzoyl]spiro [3,4-dihydropyrrolo[1,2-a]pyrazine-1,4'-piperidine]-6-yl]-2, 2,2-trifluoro-ethanone, [8-fluoro-2-methyl-6-(trifluoromethyl)spiro[3,4-dihydropyrrolo[1,2-a]pyrazine-1, 4'-piperidine]-1'-yl]-[3-methoxy-4-[(1R)-1-methylpropoxy] phenyl]methanone, 2,2,2-trifluoro-1-[1'-(5-isopropoxy-6-methyl-pyridine-2-carbonyl)-2,4-dimethyl-spiro[3,4-dihydropyrrolo[1,2-a]pyrazine-1,4'-piperidine]-6-yl] ethanone, 1-[1'-[4-methoxy-3-(trifluoromethyl)benzoyl]-2-methyl-spiro[3,4-dihydropyrrolo[1,2-a]pyrazine-1,4'-piperidine]-6-yl]-2,2-dimethyl-propan-1-one, (4-isopropoxy-3-methyl-phenyl)-[2-methyl-6-(trifluoromethyl)spiro[3,4-dihydropyrrolo[1,2-a]pyrazine-1,4'-piperidine]-1'-yl]methanone, [2-methyl-6-(1-methylcyclopropanecarbonyl)spiro[3,4-dihydropyrrolo[1,2-a]pyrazine-1,4'-piperidine]-1'-yl]-[4-(3,3,3-trifluoropropoxymethyl)phenyl] methanone, 4-bromo-N-(4-bromophenyl)-3-[(1-methyl-2-oxo-4-piperidyl)sulfamoyl]benzamide or (3-chloro-4-isopropoxy-phenyl)-[2-methyl-6-(1,1,2,2,2-pentafluoroethyl)spiro[3,4-dihydropyrrolo[1,2-a]pyrazine-1,4'-piperidine]-1'-yl]methanone.

(39) an $Na_V1.8$ blocker, such as PF-04531083, PF-06372865 and such as those disclosed in WO2008/135826 (US2009048306), WO2006/011050 (US2008312235), WO2013/061205 (US2014296313), US20130303535, WO2013131018, U.S. Pat. No. 8,466,188, WO2013114250 (US2013274243), WO2014/120808 (US2014213616), WO2014/120815 (US2014228371) WO2014/120820 (US2014221435), WO2015/010065 (US20160152561), and WO2015/089361 (US20150166589), the entire contents of each application hereby incorporated by reference.

(39a) an $Na_V1.8$ blocker such as 4,5-dichloro-2-(4-fluoro-2-methoxyphenoxy)-N-(2-oxo-1,2-dihydropyridin-4-yl) benzamide, 2-(4-fluoro-2-methoxyphenoxy)-N-(2-oxo-1,2-dihydropyridin-4-yl)-4-(perfluoroethyl)benzamide, 4,5-dichloro-2-(4-fluorophenoxy)-N-(2-oxo-1,2-dihydropyridin-4-yl)benzamide, 4,5-dichloro-2-(3-fluoro-4-methoxyphenoxy)-N-(2-oxo-1,2-dihydropyridin-4-yl) benzamide, 2-(4-fluoro-2-methoxyphenoxy)-N-(2-oxo-1,2-dihydropyridin-4-yl)-5-(trifluoromethyl)benzamide, N-(2-oxo-1,2-dihydropyridin-4-yl)-2-(4-(trifluoromethoxy) phenoxy)-4-(trifluoromethyl)benzamide, 2-(4-fluorophenoxy)-N-(2-oxo-1,2-dihydropyridin-4-yl)-4-(perfluoroethyl)benzamide, 5-chloro-2-(4-fluoro-2-methoxyphenoxy)-N-(2-oxo-1,2-dihydropyridin-4-yl) benzamide, N-(2-oxo-1,2-dihydropyridin-4-yl)-2-(4-(trifluoromethoxy)phenoxy)-5-(trifluoromethyl)benzamide, 2-(4-fluoro-2-methylphenoxy)-N-(2-oxo-1,2-dihydropyridin-4-yl)-5-(trifluoromethyl)benzamide, 2-(2-chloro-4-fluorophenoxy)-N-(2-oxo-1,2-dihydropyridin-4-yl)-5-(trifluoromethyl)benzamide, 5-chloro-2-(4-fluoro-2-methylphenoxy)-N-(2-oxo-1,2-dihydropyridin-4-yl) benzamide, 4-chloro-2-(4-fluoro-2-methylphenoxy)-N-(2-oxo-1,2-dihydropyridin-4-yl)benzamide, 5-chloro-2-(2-chloro-4-fluorophenoxy)-N-(2-oxo-1,2-dihydropyridin-4-yl)benzamide, 2-((5-fluoro-2-hydroxybenzyl)oxy)-N-(2-oxo-1,2-dihydropyridin-4-yl)-4-(trifluoromethyl) benzamide, N-(2-oxo-1,2-dihydropyridin-4-yl)-2-(o-tolyloxy)-5-(trifluoromethyl)benzamide, 2-(2,4-difluorophenoxy)-N-(2-oxo-1,2-dihydropyridin-4-yl)-4-(trifluoromethyl)benzamide, N-(2-oxo-1,2-dihydropyridin-4-yl)-2-(2-(trifluoromethoxy)phenoxy)-5-(trifluoromethyl) benzamide, 2-(4-fluorophenoxy)-N-(2-oxo-1,2-dihydropyridin-4-yl)-5-(trifluoromethyl)benzamide. In one embodiment, the compound is 3-(4-fluoro-2-methoxyphenoxy)-N-(3-(methylsulfonyl)phenyl)quinoxaline-2-carboxamide, 3-(2-chloro-4-fluorophenoxy)-N-(3-sulfamoylphenyl)quinoxaline-2-carboxamide, 3-(2-chloro-4-methoxyphenoxy)-N-(3-sulfamoylphenyl)quinoxaline-2-carboxamide, 3-(4-chloro-2-methoxyphenoxy)-N-(3-sulfamoylphenyl)quinoxaline-2-carboxamide, 4-(3-(4-(trifluoromethoxy)phenoxy)quinoxaline-2-carboxamido) picolinic acid, 2-(2,4-difluorophenoxy)-N-(3-sulfamoylphenyl)quinoline-3-carboxamide, 2-(4-fluoro-2-methoxyphenoxy)-N-(3-sulfamoylphenyl)quinoline-3-carboxamide, 3-(2,4-difluorophenoxy)-N-(3-sulfamoylphenyl)quinoxaline-2-carboxamide, N-(3-sulfamoylphenyl)-2-(4-(trifluoromethoxy)phenoxy) quinoline-3-carboxamide, N-(3-sulfamoylphenyl)-3-(4-(trifluoromethoxy)phenoxy)quinoxaline-2-carboxamide, 3-(4-chloro-2-methylphenoxy)-N-(3-sulfamoylphenyl)quinoxaline-2-carboxamide, 5-(3-(4-(trifluoromethoxy)phenoxy)quinoxaline-2-carboxamido)picolinic acid, 3-(4-fluoro-2-methoxyphenoxy)-N-(2-oxo-2,3-dihydro-1H-benzo[d]imidazol-5-yl)quinoxaline-2-carboxamide, 3-(4-fluoro-2-methoxyphenoxy)-N-(pyridin-4-yl)quinoxaline-2-carboxamide, 3-(4-fluorophenoxy)-N-(3-sulfamoylphenyl) quinoxaline-2-carboxamide, N-(3-cyanophenyl)-3-(4-fluoro-2-methoxyphenoxy)quinoxaline-2-carboxamide, N-(4-carbamoylphenyl)-3-(4-fluoro-2-methoxyphenoxy) quinoxaline-2-carboxamide, 4-(3-(4-(trifluoromethoxy)phenoxy)quinoxaline-2-carboxamido)benzoic acid, N-(4-cyanophenyl)-3-(4-fluoro-2-methoxyphenoxy)quinoxaline-2-carboxamide, 5-(4,5-dichloro-2-(4-fluoro-2-methoxyphenoxy)benzamido)picolinic acid, 5-(2-(2,4-dimethoxyphenoxy)-4,6-bis(trifluoromethyl)benzamido picolinic acid, 4-(4,5-dichloro-2-(4-fluoro-2-methoxyphenoxy)benzamido)benzoic acid, 5-(2-(4-fluoro-2-methoxyphenoxy)-4,6-bis(trifluoromethyl)benzamido) picolinic acid, 4-(2-(4-fluoro-2-methoxyphenoxy)-4-(perfluoroethyl)benzamido)benzoic acid, 5-(2-(4-fluoro-2-methoxyphenoxy)-4-(perfluoroethyl)benzamido)picolinic acid, 4-(2-(4-fluoro-2-methylphenoxy)-4-(trifluoromethyl) benzamido)benzoic acid, 5-(4,5-dichloro-2-(4-fluoro-2-methoxyphenoxy)benzamido)picolinic acid, 4-(2-(2-chloro-4-fluorophenoxy)-4-(perfluoroethyl)benzamido)benzoic acid, 4-(2-(4-fluoro-2-methoxyphenoxy)-4-(perfluoroethyl) benzamido)benzoic acid, 4-(4,5-dichloro-2-(4-(trifluoromethoxy)phenoxy)benzamido)benzoic acid, 4-(4,5-dichloro-2-(4-chloro-2-methylphenoxy)benzamido)benzoic acid, 5-(4-(tert-butyl)-2-(4-fluoro-2-methoxyphenoxy)benzamido)picolinic acid, 5-(4,5-dichloro-2-(4-(trifluoromethoxy)phenoxy)benzamido)picolinic acid, 4-(4,5-dichloro-2-(4-fluoro-2-methylphenoxy)benzamido)benzoic acid, 5-(4,5-dichloro-2-(2,4-dimethoxyphenoxy)benzamido)picolinic acid, 5-(4,5-dichloro-2-(2-chloro-4-fluorophenoxy)benzamido)picolinic acid, 5-(4,5-dichloro-2-(4-fluoro-2-methylphenoxy)benzamido)picolinic acid, 4-(4,5-dichloro-2-(4-chloro-2-methoxyphenoxy)benzamido) benzoic acid, 5-(4,5-dichloro-2-(2,4-difluorophenoxy) benzamido)picolinic acid, 2-(4-fluorophenoxy)-N-(3-sulfamoylphenyl)-5-(trifluoromethyl)benzamide, 2-(4-fluorophenoxy)-N-(3-sulfamoylphenyl)-4-(trifluoromethyl) benzamide, 2-(2-chloro-4-fluorophenoxy)-N-(3-sulfamoylphenyl)-5-(trifluoromethyl)benzamide, 2-(4-fluorophenoxy)-N-(3-sulfamoylphenyl)-4-(trifluoromethyl) benzamide, 2-(2-chloro-4-fluorophenoxy)-N-(3-sulfamoylphenyl)-6-(trifluoromethyl)benzamide, 2-(2-chloro-4-fluorophenoxy)-5-(difluoromethyl)-N-(3-sulfamoylphenyl)benzamide, 2-(4-fluorophenoxy)-4-(perfluoroethyl)-N-(3-sulfamoylphenyl)benzamide, 2-(4-chloro-2-methoxyphenoxy)-4-(perfluoroethyl)-N-(3-sulfamoylphenyl)benzamide, 2-(4-fluoro-2-methoxyphenoxy)-N-(3-sulfamoylphenyl)-5-(trifluoromethyl)benzamide, 5-chloro-2-(4-fluoro-2-methylphenoxy)-N-(3-sulfamoylphenyl)benzamide, 4,5-dichloro-2-(4-fluoro-2-methoxyphenoxy)-N-(3-sulfamoylphenyl)benzamide, 2,4-dichloro-6-(4-chloro-2-methoxyphenoxy)-N-(3-sulfamoylphenyl)benzamide, 2,4-dichloro-6-(4-fluoro-2-methylphenoxy)-N-(3-sulfamoylphenyl)benzamide, 2-(4-fluoro-2-methoxyphenoxy)-N-(3-sulfamoylphenyl)-4,6-bis (trifluoromethyl)benzamide, 2-(4-fluoro-2-methylphenoxy)-N-(3-sulfamoylphenyl)-4,6-bis(trifluoromethyl)benzamide, 5-chloro-2-(2-chloro-4-fluorophenoxy)-N-(3-sulfamoylphenyl)benzamide, 2-(4-fluoro-2-methoxyphenoxy)-N-(3-sulfamoylphenyl)-4-(trifluoromethoxy)benzamide, 2-(4-fluoro-2-methoxyphenoxy)-N-(3-sulfamoylphenyl)-4-(trifluoromethyl)benzamide, 4,5-dichloro-2-(4-fluorophenoxy)-N-(3-sulfamoylphenyl)benzamide, 2-(4-fluoro-2-methoxyphenoxy)-4-(perfluoroethyl)-N-(3-sulfamoylphenyl)benzamide, 5-fluoro-2-(4-fluoro-2-methylphenoxy)-N-(3-sulfamoylphenyl)benzamide, 2-(2-chloro-4-fluorophenoxy)-4-cyano-N-(3-sulfamoylphenyl) benzamide or N-(3-sulfamoylphenyl)-2-(4-(trifluoromethoxy)phenoxy)-4-(trifluoromethyl)benzamide.

(40) a combined $Na_V1.7$ and $Na_V1.8$ blocker, such as DSP-2230 or BL-1021;

(41) a 5-HT3 antagonist, such as ondansetron;

(42) a TPRV 1 receptor agonist, such as capsaicin (NeurogesX®, Qutenza®); and the pharmaceutically acceptable salts and solvates thereof;

(43) a nicotinic receptor antagonist, such as varenicline;

(44) an N-type calcium channel antagonist, such as Z-160;

(45) a nerve growth factor antagonist, such as tanezumab;

(46) an endopeptidase stimulant, such as senrebotase;

(47) an angiotensin II antagonist, such as EMA-401;

In one embodiment, the additional appropriate therapeutic agents are selected from V-116517, Pregabalin, controlled release Pregabalin, Ezogabine (Potiga®). Ketamine/amitriptyline topical cream (Amiket®), AVP-923, Perampanel (E-2007), Ralfinamide, transdermal bupivacaine (Eladur®), CNV1014802, JNJ-10234094 (Carisbamate), BMS-954561 or ARC-4558.

In another embodiment, the additional appropriate therapeutic agents are selected from N-(6-amino-5-(2,3,5-trichlorophenyl)pyridin-2-yl)acetamide; N-(6-amino-5-(2-chloro-5-methoxyphenyl)pyridin-2-yl)-1-methyl-1H-pyrazole-5-carboxamide; or 3-((4-(4-(trifluoromethoxy)phenyl)-1H-imidazol-2-yl)methyl)oxetan-3-amine.

In another embodiment, the additional therapeutic agent is a sodium channel inhibitor (also know as a sodium channel blocker), such as the $Na_V1.7$ and $Na_V1.8$ blockers identified above.

The amount of additional therapeutic agent present in the compositions of this invention may be no more than the amount that would normally be administered in a composition comprising that therapeutic agent as the only active agent. The amount of additional therapeutic agent in the presently disclosed compositions may range from about 10% to 100% of the amount normally present in a composition comprising that agent as the only therapeutically active agent.

The compounds and salts of this invention or pharmaceutically acceptable compositions thereof may also be incorporated into compositions for coating an implantable medical device, such as prostheses, artificial valves, vascular grafts, stents and catheters. Accordingly, the invention, in another aspect, includes a composition for coating an implantable device comprising a compound or salt of the invention as described generally above, and in classes and subclasses herein, and a carrier suitable for coating said implantable device. In still another aspect, the invention includes an implantable device coated with a composition comprising a compound or salt of the invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

Another aspect of the invention relates to inhibiting $Na_V1.8$ activity in a biological sample or a subject, which method comprises administering to the subject, or contacting said biological sample with a compound of the invention, a pharmaceutically acceptable salt thereof, or a pharmaceutical composition thereof. The term "biological sample," as used herein, includes, without limitation, cell cultures or extracts thereof; biopsied material obtained from a mammal or extracts thereof; and blood, saliva, urine, feces, semen, tears, or other body fluids or extracts thereof.

Inhibition of $Na_V1.8$ activity in a biological sample is useful for a variety of purposes that are known to one of skill in the art. Examples of such purposes include, but are not limited to, the study of sodium channels in biological and pathological phenomena; and the comparative evaluation of new sodium channel inhibitors.

EXAMPLES

General methods. $^1H$ NMR (400 MHz) spectra were obtained as solutions in an appropriate deuterated solvent such as dimethyl sulfoxide-$d_6$ (DMSO-$d_6$).

Compound purity, retention time, and electrospray mass spectrometry (ESI-MS) data were determined by LC/MS analysis using one of two methods: Method A and Method B.

LC/MS Method A. LC/MS analysis was conducted using a Waters Acquity Ultra Performance LC system by reverse phase UPLC using an Acquity UPLC BEH C18 column (30×2.1 mm, 1.7 µm particle) made by Waters (pn:

186002349), and a dual gradient run from 1-99% mobile phase B over 1.2 minutes. Mobile phase A=H$_2$O (0.05% CF$_3$CO$_2$H). Mobile phase B=CH$_3$CN (0.035% CF$_3$CO$_2$H). Flow rate=1.5 mL/min, injection volume=1.5 µL, and column temperature=60° C.

LC/MS Method B. LC/MS analysis was conducted using a Waters Acquity Ultra Performance LC system by reverse phase UPLC using an Acquity UPLC BEH C18 column (50×2.1 mm, 1.7 µm particle) made by Waters (pn: 186002350), and a dual gradient run from 1-99% mobile phase B over 3.0 minutes. Mobile phase A=H$_2$O (0.05% CF3CO2H). Mobile phase B=CH$_3$CN (0.035% CF$_3$CO$_2$H). Flow rate=1.2 mL/min, injection volume=1.5 µL, and column temperature=60° C.

Abbreviations

Unless otherwise noted, or where the context dictates otherwise, the following abbreviations shall be understood to have the following meanings:

| Abbreviation | Meaning |
| --- | --- |
| NMR | Nuclear magnetic resonance |
| MHz | Megahertz |
| DMSO | Dimethyl sulfoxide |
| ESI-MS | Electrospray mass spectrometry |
| m/z | Mass-to-Charge Ratio |
| LC/MS | Liquid chromatography-mass spectrometry |
| LC/MS-MS | Liquid chromatography-tandem mass spectrometry |
| UPLC | Ultra performance liquid chromatography |
| mL | Milliliters |
| min | Minutes |
| hr | Hour |
| µL | Microliters |
| mm | Millimeters |
| µm | Micrometers |
| THF | Tetrahydrofuran |
| n-BuLi | n-butyl lithium |
| DCM | Dichloromethane |
| T3P | Propylphosphonic anhydride |
| TEA | triethylamine |
| 2-MeTHF | 2-methyltetrahydrofuran |
| AcOH, HOAc | Acetic acid |
| DABCO | 1,4-diazabicyclo[2.2.2]octane |
| DCE | 1,2-dichloroethane |
| DMF | N,N-dimethylformamide |
| Bu$_4$NI | Tetrabutylammonium iodide |
| EtOAc | Ethyl acetate |
| iPrOH | Isopropyl alcohol |
| g | grams |
| M | Molar (concentration) |
| mmol | millimoles |
| mg | milligrams |
| N | Normal (concentration) |
| aq | Aqueous |
| ppm | Parts per million |
| E-VIPR | Electrical stimulation voltage ion probe reader |
| HEK | Human embryonic kidney |
| KIR2.1 | Inward-rectifier potassium ion channel 2.1 |
| DMEM | Dulbecco's Modified Eagle's Medium |
| FBS | Fetal bovine serum |
| NEAA | Non-essential amino acids |
| HEPES | 2-[4-(2-hydroxyethyl)piperazin-1-yl]ethanesulfonic acid |
| DiSBAC$_6$(3) | Bis-(1,3-dihexyl-thiobarbituric acid) trimethine oxonol |
| CC2-DMPE | Chlorocoumarin-2-dimyristoyl phosphatidylethanolamine |
| VABSC-1 | Voltage Assay Background Suppression Compound |
| HS | Human serum |
| L | Liter(s) |
| BSA | Bovine Serum Albumin |
| nL | nanoliters |
| ms | millisecond |
| Hz | Hertz |
| nm | nanometer |
| NADPH | Nicotinamide adenine dicnucleotide phosphate, reduced form |
| ACN | Acetonitrile |
| mM | Millimolar (concentration) |
| µM | Micromolar (concentration) |
| HPLC/MS/MS | High performance liquid chromatography/tandem mass spectrometry |
| IS | Internal standard |
| HPLC | High performance liquid chromatography |
| MRM | Multiple reaction monitoring |
| ESI | Electrospray ionization |
| LLOQ | Lower limit of quantitation |
| AUC$_{all}$ | Area under the plasma drug concentration-versus-time curve from the time of drug administration (time zero) to the last time point with measurable drug concentration |
| AUC$_{0-\infty}$ | Area under the plasma drug concentration-versus-time curve from the time of drug administration (time zero) extrapolated to time infinity |
| C$_0$ | Concentration just after intravenous administration (at time zero) |
| Cl | Clearance |
| Vss | Volume of distribution at steady state |
| t$_{1/2}$ | Half-life |
| SD | Standard deviation |
| % CV | Coefficient of variation |
| D5W | 5% dextrose in water |
| PK | Pharmacokinetic |
| rpm | Revolutions per minute |

Example 1

2-(4-fluoro-2-methylphenoxy)-N-(2-oxo-1,2-dihydropyridin-4-yl)-4-(trifluoromethyl)benzamide (10)

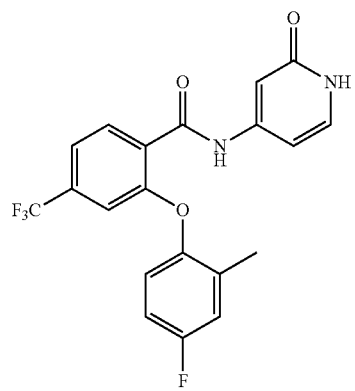

10

A synthesis of 2-(4-fluoro-2-methylphenoxy)-N-(2-oxo-1,2-dihydropyridin-4-yl)-4-(trifluoromethyl)benzamide (10) is described in International Publication No. WO 2014/120808 A9 and U.S. Publication No. 2014/0213616 A1, both of which are incorporated by reference in their entirety.

Example 2

(4-(2-(4-fluoro-2-methylphenoxy)-4-(trifluoromethyl)benzamido)-2-oxopyridin-1(2H)-yl)methyl dihydrogen phosphate (20)

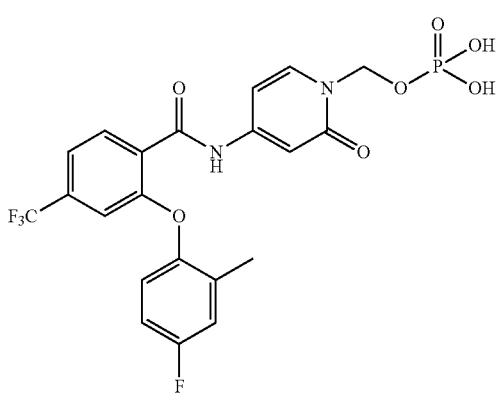

20

A synthesis of (4-(2-(4-fluoro-2-methylphenoxy)-4-(trifluoromethyl)benzamido)-2-oxopyridin-1(2H)-yl)methyl dihydrogen phosphate (20) is described in International Publication No. WO 2015/089361 A1 and US Publication No. 2015/0166589 A1, both of which are incorporated by reference in their entirety.

Example 3

2-(4-fluoro-2-(methyl-$d_3$)phenoxy)-N-(2-oxo-1,2-dihydropyridin-4-yl)-4-(trifluoromethyl)benzamide (7)

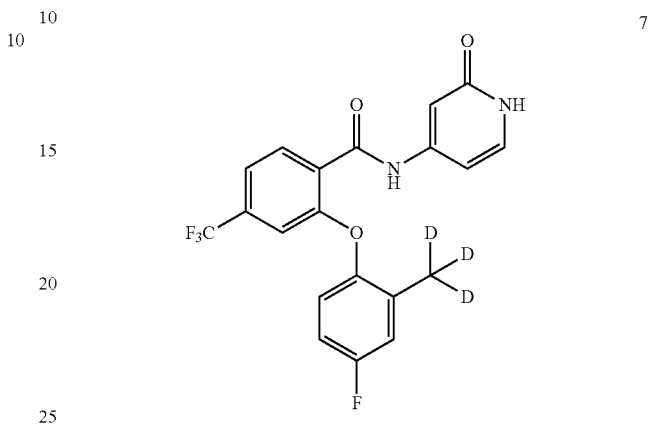

7

2-(4-fluoro-2-(methyl-$d_3$)phenoxy)-N-(2-oxo-1,2-dihydropyridin-4-yl)-4-(trifluoromethyl)benzamide (7) was synthesized as shown in Scheme 1. Trideuteromethylation of 1-fluoro-4-methoxy-benzene (1) afforded 4-fluoro-1-methoxy-2-(methyl-$d_3$)benzene (2), which underwent demethylation to afford 4-fluoro-2-(methyl-$d_3$)phenol (3). Separately, coupling of 2-fluoro-4-(trifluoromethyl)benzoic acid (4) with 2-methoxypyridin-4-amine afforded 2-fluoro-N-(2-methoxy-4-pyridyl)-4-(trifluoromethyl)benzamide (5), which underwent demethylation to afford 2-fluoro-N-(2-oxo-1H-pyridin-4-yl)-4-(trifluoromethyl)benzamide (6). 2-Fluoro-N-(2-oxo-1H-pyridin-4-yl)-4-(trifluoromethyl) benzamide (6) was treated with 4-fluoro-2-(methyl-$d_3$)phenol (3) in the presence of base to afford 2-(4-fluoro-2-(methyl-$d_3$)phenoxy)-N-(2-oxo-1,2-dihydropyridin-4-yl)-4-(trifluoromethyl)benzamide (7). Detailed experimental procedures and analytical data are provided below.

Scheme 1. Synthesis of Compound 7

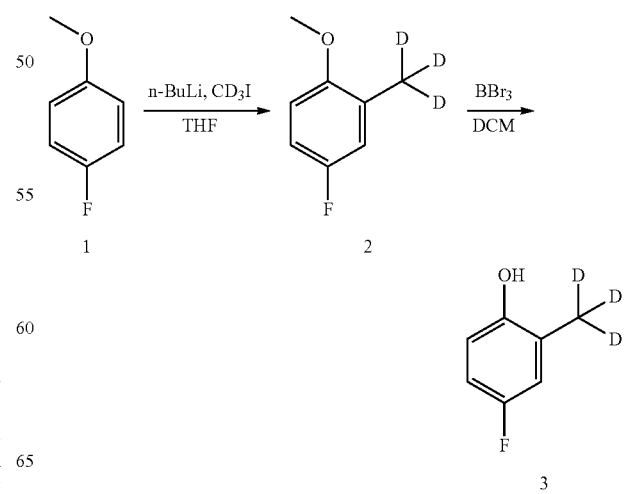

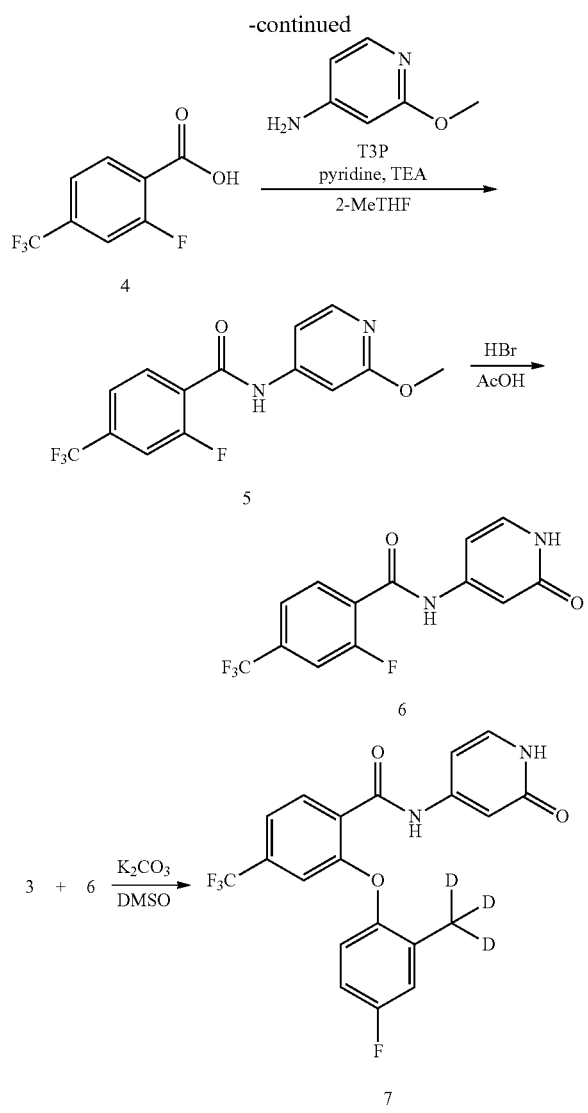

Preparation of 4-fluoro-2-(methyl-d₃)phenol (3). To a solution of 1-fluoro-4-methoxy-benzene (1) (1.02 g, 8.09 mmol) in THF (10 mL) at −10° C. was added n-BuLi (2.38 g of 2.5 M in hexane, 8.75 mmol) over 20 minutes while maintaining internal temperature below −5° C. The solution was allowed to warm to room temperature and then stirred for 1 hour. The mixture was cooled to 0° C. and treated dropwise with iodomethane-d₃ (1.30 g, 8.97 mmol, 99.5% D incorporation) while maintaining an internal temperature under 5° C. The reaction was allowed to come to room temperature and stirred for 45 minutes. The reaction mixture was diluted with diethyl ether and cold water, and the layers separated. The aqueous layer was extracted with additional ether, and the combined organic layers were washed with brine, dried over sodium sulfate, filtered and concentrated. Silica gel chromatography (0-10% ethyl acetate/hexane) provided 4-fluoro-1-methoxy-2-(methyl-d₃)benzene (2) (160 mg, 14%). $^1$H NMR (400 MHz, DMSO-d₆) δ 7.03-6.97 (m, 1H), 6.95 (dd, J=8.4, 3.2 Hz, 1H), 6.90 (dd, J=8.9, 4.8 Hz, 1H), 3.76 (s, 3H) ppm. LC/MS retention time (Method A): 0.60 minutes (1 minute run).

To a solution of 4-fluoro-1-methoxy-2-(methyl-d₃)benzene (2) (160 mg, 1.12 mmol) in dichloromethane (2 mL) at 0° C. was added BBr₃ (2.3 mL of 1 M in dichloromethane, 2.3 mmol) dropwise over 5 minutes. The reaction was removed from the ice bath, allowed to come to room temperature and stirred for 1 hour. The reaction mixture was diluted with dichloromethane and washed with water and brine. The organic layer was dried over sodium sulfate, filtered and concentrated to provide crude 4-fluoro-2-(methyl-d₃)phenol (3) (125 mg, 87%) which was used directly in the next reaction. LC/MS retention time (Method A): 0.43 minutes (1 minute run).

Preparation of 2-fluoro-N-(2-oxo-1,2-dihydropyridin-4-yl)-4-(trifluoromethyl)benzamide (6). A solution of 2-fluoro-4-(trifluoromethyl)benzoic acid (4) (5.0 g, 24 mmol) in 2-methyltetrahydrofuran (30 mL) at 40° C. was treated with T3P solution (23 mL of 50% w/v in ethyl acetate, 36 mmol) followed by pyridine (5.7 g, 5.8 mL, 72 mmol), triethylamine (7.3 g, 10 mL, 72 mmol) and 2-methoxypyridin-4-amine (3.3 g, 26 mmol). The reaction was heated at 40° C. for 16 hours. Water (50 mL) was added and the mixture stirred. The resulting layers were separated, and the organic layer was washed with 50 mL 0.1 N HCl, 50 mL 10% KOH and 50 mL brine. The solution was dried over sodium sulfate, filtered and evaporated to provide 2-fluoro-N-(2-methoxy-4-pyridyl)-4-(trifluoromethyl)benzamide (5) (7.1 g, 94%). ESI-MS m/z calc. 314.07, found 315.2 (M+1)+. LC/MS retention time (Method B): 1.21 minutes (3 minute run). $^1$H NMR (400 MHz, DMSO-d₆) δ 10.96 (s, 1H), 8.14-8.07 (m, 1H), 7.96-7.88 (m, 2H), 7.76 (dd, J=8.1, 1.6 Hz, 1H), 7.22 (d, J=4.7 Hz, 2H), 3.85 (s, 3H) ppm.

To a suspension of 2-fluoro-N-(2-methoxy-4-pyridyl)-4-(trifluoromethyl)benzamide (5) (6.44 g, 20.5 mmol) in acetic acid (39 mL) was added HBr in acetic acid (25 mL of 33% w/v, 103 mmol) and the reaction was stirred at 100° C. for 16 hours. The reaction mixture was cooled to 28° C. and treated with toluene (15 mL). The mixture was stirred for 10 minutes, filtered, and the resulting solid washed with toluene (15 mL) and dried under vacuum at 40° C. to provide 3.42 g of product. Second (0.35 g) and third (0.40 g) crops of product were obtained by sequential filtration of the mother liquor and rinsing the resulting solid with toluene (15 mL). The solids were combined to obtain 2-fluoro-N-(2-oxo-1H-pyridin-4-yl)-4-(trifluoromethyl)benzamide (6) (4.17 g, 70%). ESI-MS m/z calc. 300.05, found 301.1 (M+1)+. LC/MS retention time (Method B): 1.05 minutes (3 minute run). $^1$H NMR (400 MHz, DMSO-d₆) δ 11.81 (br s, 1H), 10.86 (s, 1H), 7.96-7.87 (m, 2H), 7.76 (dd, J=8.2, 1.6 Hz, 1H), 7.48 (dd, J=7.1, 1.8 Hz, 1H), 6.96 (d, J=2.1 Hz, 1H), 6.56 (dd, J=7.2, 2.1 Hz, 1H) ppm.

Preparation of 2-(4-fluoro-2-(methyl-d₃)phenoxy)-N-(2-oxo-1,2-dihydropyridin-4-yl)-4-(trifluoromethyl)benzamide (7). 2-Fluoro-N-(2-oxo-1H-pyridin-4-yl)-4-(trifluoromethyl)benzamide (6) (265 mg, 0.883 mmol), K₂CO₃ (366 mg, 2.645 mmol) and 4-fluoro-2-(methyl-d₃)phenol (3) (125 mg, 0.968 mmol) were combined in anhydrous DMSO (2.5 mL) and heated at 75° C. for 16 hours. The reaction was diluted with water (10 mL), filtered, and the resulting solid washed with water (10 mL) and air dried. The solid was slurried in isobutyl acetate and filtered to provide the desired product as an off-white solid (200 mg). The mother liquor was concentrated and purified by silica gel chromatography (1-15% methanol/dichloromethane) to provide an additional 60 mg of product. The two crops were dissolved in dichloromethane, the solvent concentrated and the resulting solid air dried to provide 2-(4-fluoro-2-(methyl-d₃)phenoxy)-N-(2-oxo-1,2-dihydropyridin-4-yl)-4-(trifluoromethyl)benzamide (7) (260 mg, 72%). ESI-MS m/z calc. 409.11, found 410.2 (M+1)⁺. LC/MS retention time (Method B): 1.59 minutes (3 minute run). $^1$H NMR (400 MHz, DMSO-d$_6$) δ 11.26 (s, 1H), 10.61 (s, 1H), 7.88-7.78 (m, 1H), 7.60 (dt, J=8.1, 1.1 Hz, 1H), 7.31 (d, J=7.2 Hz, 1H), 7.22 (ddd, J=9.2, 2.5, 1.0 Hz, 1H), 7.12-7.07 (m, 2H), 6.97 (d, J=1.6 Hz, 1H), 6.75 (d, J=2.0 Hz, 1H), 6.38 (dd, J=7.2, 2.1 Hz, 1H) ppm.

Example 4

(4-(2-(4-fluoro-2-(methyl-d$_3$)phenoxy)-4-(trifluoromethyl)benzamido)-2-oxopyridin-1(2H)-yl)methyl dihydrogen phosphate (13)

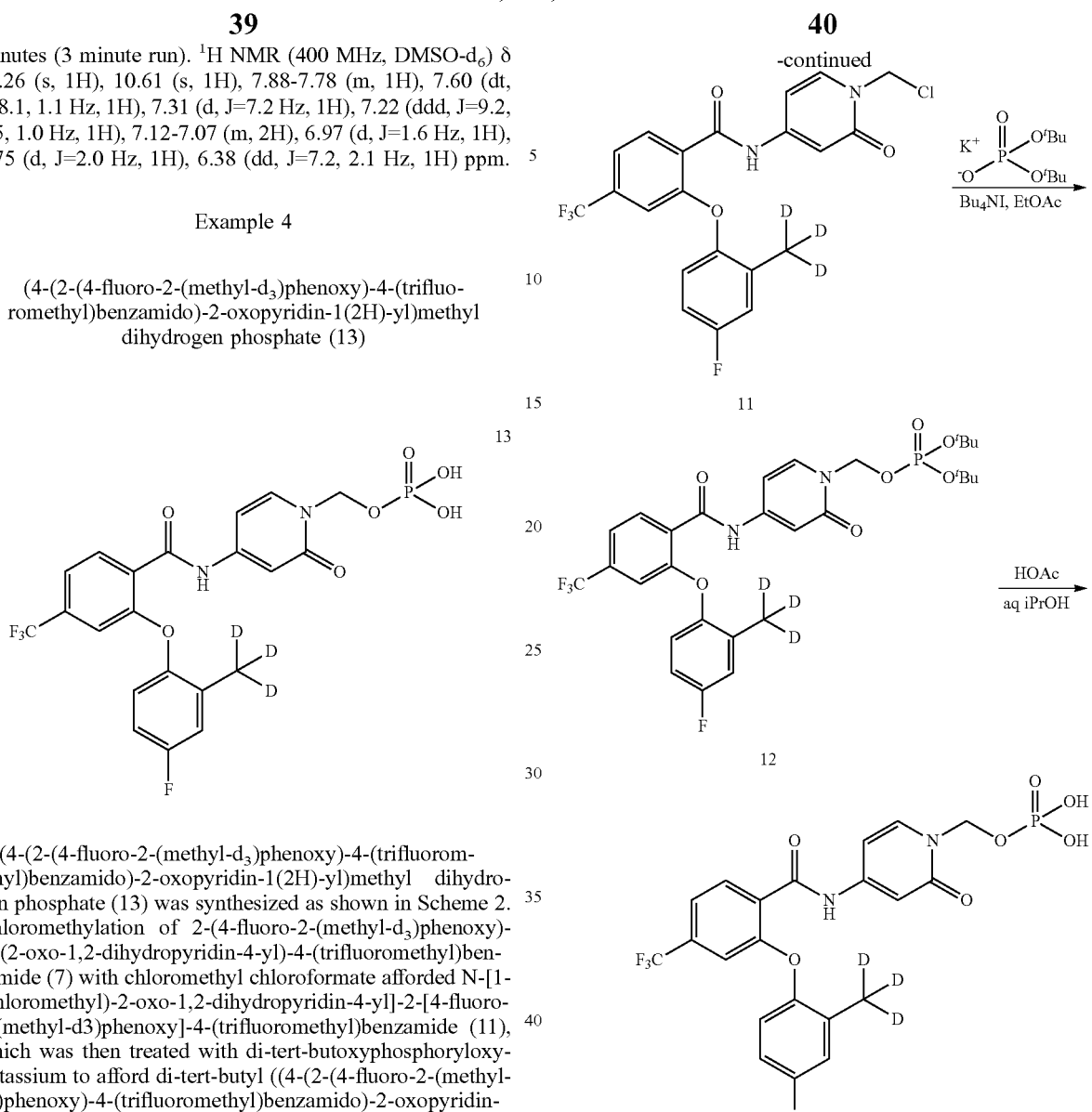

(4-(2-(4-fluoro-2-(methyl-d$_3$)phenoxy)-4-(trifluoromethyl)benzamido)-2-oxopyridin-1(2H)-yl)methyl dihydrogen phosphate (13) was synthesized as shown in Scheme 2. Chloromethylation of 2-(4-fluoro-2-(methyl-d$_3$)phenoxy)-N-(2-oxo-1,2-dihydropyridin-4-yl)-4-(trifluoromethyl)benzamide (7) with chloromethyl chloroformate afforded N-[1-(chloromethyl)-2-oxo-1,2-dihydropyridin-4-yl]-2-[4-fluoro-2-(methyl-d3)phenoxy]-4-(trifluoromethyl)benzamide (11), which was then treated with di-tert-butoxyphosphoryloxypotassium to afford di-tert-butyl ((4-(2-(4-fluoro-2-(methyl-d$_3$)phenoxy)-4-(trifluoromethyl)benzamido)-2-oxopyridin-1(2H)-yl)methyl) phosphate (12). Hydrolysis of compound 12 afforded (4-(2-(4-fluoro-2-(methyl-d3)phenoxy)-4-(trifluoromethyl)benzamido)-2-oxopyridin-1(2H)-yl)methyl dihydrogen phosphate (13). Detailed experimental procedures and analytical data are provided below.

Scheme 2. Synthesis of Compound 13

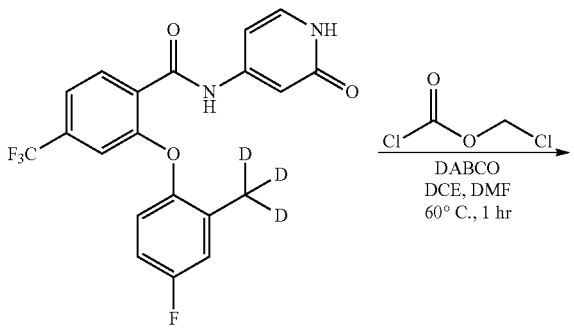

Preparation of N-[1-(chloromethyl)-2-oxo-1,2-dihydropyridin-4-yl]-2-[4-fluoro-2-(methyl-d3)phenoxy]-4-(trifluoromethyl)benzamide (11). To a slurry of 2-(4-fluoro-2-(methyl-d$_3$)phenoxy)-N-(2-oxo-1,2-dihydropyridin-4-yl)-4-(trifluoromethyl)benzamide (7) (1.9 g, 4.642 mmol) in DCE (20 mL) and DMF (1 mL) was added DABCO (265 mg, 2.362 mmol). To the slurry was added chloromethyl chloroformate (620 μL, 6.972 mmol) dropwise over 5 min. The mixture was stirred at 60° C. for 1 hr. The light yellow slurry was cooled to ambient temperature and diluted with water (50 mL) and DCM (50 mL). The organic phase was separated and the aqueous phase was extracted with DCM (50 mL). The combined organic phases were washed with brine. The organic phase was dried over MgSO$_4$, filtered over celite and concentrated affording N-[1-(chloromethyl)-2-oxo-1,2-dihydropyridin-4-yl]-2-[4-fluoro-2-(methyl-d$_3$)phenoxy]-4-(trifluoromethyl)benzamide (11) (2.1 g, 99%). The product was used without further purification in the next step. ESI-MS m/z calc. 457.08957, found 458.1 (M+1)$^+$; LC/MS retention time (Method B): 2.06 minutes (3 minute run).

Preparation of di-tert-butyl ((4-(2-(4-fluoro-2-(methyl-d3)phenoxy)-4-(trifluoromethyl)benzamido)-2-oxopyridin-1(2H)-yl)methyl) phosphate (12). To a suspension of N-[1-(chloromethyl)-2-oxo-1,2-dihydropyridin-4-yl]-2-[4-fluoro-2-(methyl-d3)phenoxy]-4-(trifluoromethyl)benzamide (11) (2.1 g, 4.587 mmol) in EtOAc (25 mL) was added tetra-butylammonium iodide (30 mg, 0.08122 mmol) followed by di-tert-butoxyphosphoryloxypotassium (1.3 g, 5.236 mmol) and the mixture heated to 70° C. for 3 hr. The reaction was quenched by pouring over ice water (50 mL) and diluting with EtOAc (100 mL). The organic phase was separated and washed with brine. The aqueous phases were extracted with EtOAc (100 mL) and the combined organic phases were dried over $MgSO_4$, filtered and concentrated. The crude product was purified using reverse phase chromatography (50-100% water/ACN) affording di-tert-butyl ((4-(2-(4-fluoro-2-(methyl-d$_3$)phenoxy)-4-(trifluoromethyl)benzamido)-2-oxopyridin-1(2H)-yl)methyl) phosphate (12) (1.75 g, 60%). ESI-MS m/z calc. 631.21497, found 632.2 (M+1)$^+$; LC/MS retention time (Method B): 2.25 minutes (3 minute run).

Preparation of (4-(2-(4-fluoro-2-(methyl-d3)phenoxy)-4-(trifluoromethyl)benzamido)-2-oxopyridin-1(2H)-yl)methyl dihydrogen phosphate (13). To a mixture of di-tert-butyl ((4-(2-(4-fluoro-2-(methyl-d3)phenoxy)-4-(trifluoromethyl)benzamido)-2-oxopyridin-1(2H)-yl)methyl) phosphate (12) (1.5 g, 2.375 mmol) in isopropanol (9 mL) and water (3 mL) was added HOAc (4.5 mL). The mixture was heated at 70° C. for 4.5 hr. The mixture was concentrated to approximately 2 mL of oil and diluted with 10 mL ACN affording a hazy solution which was further diluted with 10 mL of isopropanol. The solvent was concentrated to approximately 2 mL which afforded a granular solid. The solid was collected using a medium fritted funnel and washed 3× with 5 mL of acetone. The solid was air dried for 15 min, then in a vacuum oven at 40° C. for 16 hours affording (4-(2-(4-fluoro-2-(methyl-d$_3$)phenoxy)-4-(trifluoromethyl)benzamido)-2-oxopyridin-1(2H)-yl)methyl dihydrogen phosphate (13) (150 mg, 12%). ESI-MS m/z calc. 519.0898, found 520.0 (M+1)$^+$; LC/MS retention time (Method B): 1.99 minutes (3 minute run). $^1$H NMR (400 MHz, DMSO-d$_6$) δ 11.51 (s, 2H), 10.75 (s, 1H), 7.86 (d, J=7.9 Hz, 1H), 7.61 (dd, J=7.2, 1.7 Hz, 2H), 7.22 (ddd, J=9.3, 2.5, 1.0 Hz, 1H), 7.15-7.06 (m, 2H), 6.98 (d, J=1.5 Hz, 1H), 6.89 (d, J=2.3 Hz, 1H), 6.44 (dd, J=7.6, 2.3 Hz, 1H), 5.53 (d, J=9.7 Hz, 2H) ppm.

Example 5

Evaluation of Prodrug Conversion to Parent Compound: In Vitro Hepatocyte Assay

Materials. Cryopreserved human hepatocytes and Cryopreserved Hepatocytes Recovery Medium (CHRM™) were purchased from Life Technologies (Carlsbad, Calif.). Gibco™ Leibovitz's L-15 Medium was purchased from Fisher Scientific (Waltham, Mass.).

Methods. 10 mM stock solutions containing Compound 20 and Compound 13 were prepared in DMSO. Equal volumes of the two 10 mM stock solutions were mixed to form a combination stock solution containing Compound 20 and Compound 13 in concentrations of 5 mM each. The 5 mM combination stock solution was diluted to a concentration of 50 µM of each compound in DMSO ("50 µM combination stock"). Cryopreserved human hepatocytes were thawed in CHRM™ medium and prepared as a suspension in incubation medium (L-15 Medium with supplements containing glucose, HEPES buffer and $NaHCO_3$), with the final cell concentration of 0.625 million cells/mL. In a 48 well plate, 1 µL of the 50 µM combination stock and then 199 µL of hepatocyte suspension (0.625 million cells/mL) were added to each well. The plate was covered and incubated at 37° C. in an incubator with gentle shaking (50 rpm). The reactions were quenched at 0, 0.25, 0.5, 1 and 2 hours by adding 200 µL of ice-cold quench solution (ACN:MeOH:0.1% aqueous formic acid, 2:2:1) containing internal standard (n=3 per time point). The quenched samples were centrifuged, and the supernatants were analyzed for the amount of Compound 20 and Compound 13 remaining, and the amount of Compound 10 and Compound 7 formed, by LC-MS/MS analysis. LC-MS/MS analysis was conducted using a Phenomenex Luna C8 column (3 micron, 2 mm diameter×30 mm long, at room temperature) eluted with a gradient consisting of mobile phases of 0.1% formic acid in water and 0.1% formic acid in acetonitrile at a total flow rate of 0.6 mL/min and a total run time of 4.5 minutes. The analytes were detected by MS/MS with Electrospray Ionization (ESI) in the mode of multiple reaction monitoring (MRM). The injection volume was 10 µL.

Results. When the samples of Compound 20 and Compound 13 incubated with human hepatocytes were analyzed by LC-MS/MS analysis, the peaks corresponding to Compound 20 and Compound 13 decreased quickly, with a concomitant increase in the peaks corresponding to Compound 10 and Compound 7, indicating fast conversion of Compound 20 and Compound 13 to Compound 10 and Compound 7, respectively. The $t_{1/2}$ of Compound 20 and Compound 13 in human hepatocytes were <0.5 hr. The percentages of Compound 20 and Compound 13 remaining at each time point during incubation with human hepatocytes are reported in Table 1.

TABLE 1

Percentages of Compound 20 and Compound 13 Remaining during Hepatocyte Assay

| Time (hr) | % Remaining (Compound 20) | % Remaining (Compound 13) |
|---|---|---|
| 0 | 100 | 100 |
| 0.25 | 75.1 | 73.8 |
| 0.5 | 32.7 | 33.2 |
| 1 | 11.2 | 11.1 |
| 2 | 11.6 | 11.8 |

Example 6

E-VIPR Assay for Detecting and Measuring $Na_V$ Inhibition Properties

Sodium ion channels are voltage-dependent proteins that can be activated by inducing membrane voltage changes by applying electric fields. The electrical stimulation instrument and methods of use, referred to as E-VIPR, are described in International Publication No. WO 2002/008748 A3 and C.-J. Huang et al. *Characterization of voltage-gated sodium channel blockers by electrical stimulation and fluorescence detection of membrane potential*, 24 Nature Biotech. 439-46 (2006), both of which are incorporated by reference in their entirety. The instrument comprises a microtiter plate handler, an optical system for exciting the coumarin dye while simultaneously recording the coumarin and oxonol emissions, a waveform generator, a current- or voltage-controlled amplifier, and parallel electrode pairs that are inserted into assay plate wells. Under integrated computer control, this instrument passes user-programmed electrical stimulus protocols to cells within the wells of the microtiter plate.

16-20 Hours prior to running the assay on E-VIPR, HEK cells expressing human $Na_V 1.8$ were seeded into 384-well plates (Greiner #781091-1B), pre-coated with matrigel, at a density of 25,000 cells per well. 5% KIR2.1 Bacmam virus was added to the final cell suspension before seeding into cell plates. HEK cells were grown in DMEM media (exact composition is specific to each cell type and $Na_V$ subtype) supplemented with 10% FBS (Fetal Bovine Serum, qualified; Sigma #F4135), 1% NEAA (Non-Essential Amino Acids, Life Tech #11140), 1% HEPES (Life Tech #15630), 1% Pen-Strep (Penicillin-Streptomycin; Life Tech #15640) and 5 μg/ml Blasticidin (Gibco #R210-01). Cells were expanded in vented cap flasks, with 95% humidity and 5% $CO_2$.

Reagents and Stock Solutions:
100 mg/mL Pluronic F-127 (Sigma #P2443), in dry DMSO Compound Plates: Corning 384-well Polypropylene Round Bottom #3656

Cell Plates: 384-well tissue culture treated plates. Greiner #781091-1B

5% KIR 2.1 Bacmam virus (produced in-house), prepared as described in Section 3.3 of J. A. Fornwald et al., *Gene Expression in Mammalian Cells Using BacMam, a Modified Baculovirus System*, 1350 Methods in Molecular Biology 95-116 (2016), the entire contents of which are incorporated by reference.

5 mM $DiSBAC_6(3)$ (a voltage sensitive oxonol acceptor) (Aurora #00-100-010) in dry DMSO 5 mM CC2-DMPE (a membrane-bound coumarin phospholipid FRET donor) (Aurora #00-100-008) in dry DMSO 89 mM VABSC-1 in $H_2O$ Human Serum (HS, Millipore #S1P1-01KL, lot #2706671A)

Bath1 Buffer:
Sodium Chloride 160 mM (9.35 g/L), Potassium Chloride, 4.5 mM (0.335 g/L), Glucose 10 mM (1.8 g/L), Magnesium Chloride (Anhydrous) 1 mM (0.095 g/L), Calcium Chloride 2 mM (0.222 g/L), HEPES 10 mM (2.38 g/L) in water.

Na/TMA Cl Bath1 Buffer:
Sodium Chloride 96 mM (5.61 g/L), Potassium Chloride 4.5 mM (0.335 g/L), Tetramethylammonium (TMA)-Cl 64 mM (7.01 g/L), Glucose 10 mM (1.8 g/L), Magnesium Chloride (Anhydrous) 1 mM (0.095 g/L), Calcium Chloride 2 mM (0.222 g/L) HEPES 10 mM (2.38 g/L) in water.

Hexyl Dye Solution (2×):
Bath1 Buffer containing 0.5% β-cyclodextrin (made fresh prior to each use, Sigma #C4767), 8 μM CC2-DMPE and 2 μM $DiSBAC_6(3)$. The solution was made by adding 10% Pluronic F127 stock equal to combined volumes of CC2-DMPE and $DiSBAC_6(3)$. The order of preparation was first mix Pluronic and CC2-DMPE, then add $DiSBAC_6(3)$, then while vortexing add Bath1/β-Cyclodextrin.

Compound Loading Buffer (2×): Na/TMA Cl Bath1 Buffer containing HS 50% (omitted in experiments run in the absence of HS), VABSC-1 1 mM, BSA 0.2% (in Bath-1), KCl 9 mM, DMSO 0.75%.

Assay Protocol:
1) 400 nL of the test compound (Compound 7 or Compound 13) was pre-spotted (in neat DMSO) into polypropylene compound plates at 400× desired final concentration, in an 11 point dose response, 3-fold dilution, resulting in a top dose of 3 μM final concentration in the cell plate. Vehicle control (neat DMSO), and positive control (Compound 10 (for assay with Compound 7) or Compound 20 (for assay with Compound 13), 25 μM final in assay in DMSO) were added manually to the outermost columns of each plate respectively. The compound plate was backfilled with 80 μl per well of Compound Loading Buffer resulting in a 400 fold dilution of compound following a 1:1 transfer of compound into the cell plate (Step 6). Final DMSO concentration for all wells in the assay was 0.625% (0.75% DMSO was supplemented to the Compound Loading Buffer for a final DMSO concentration of 0.625%).

2) Hexyl Dye Solution was prepared.
3) Cell plates were prepared. On the day of the assay, the media was aspirated, and the cells were washed three times with 80 μL of Bath-1 buffer, maintaining 25 μL residual volume in each well.

4) 25 μL per well of Hexyl Dye Solution was dispensed into the cell plates. The cells were incubated for 20 minutes at room temp or ambient conditions in darkness.

5) 80 μL per well of Compound Loading Buffer was dispensed into compound plates.

6) The cell plates were washed three times with 80 μL per well of Bath-1 Buffer, leaving 25 μL of residual volume. Then 25 μL per well from compound plate was transferred to each cell plate. The mixture was incubated for 30 minutes at room temp/ambient conditions.

7) The plate was read on E-VIPR using the current-controlled amplifier to deliver stimulation wave pulses using the following protocol: 1.25 Amps, 2.5 ms pulse width biphasic waveform, 10 Hz for 10 seconds at a scan rate of 200 Hz. A pre-stimulus recording was performed for 0.5 seconds to obtain the un-stimulated intensities baseline. The stimulatory waveform was followed by 0.5 seconds of post-stimulation recording to examine the relaxation to the resting state.

Data Analysis:
Data were analyzed and reported as normalized ratios of emission intensities measured in the 460 nm and 580 nm channels. The response as a function of time was reported as the ratios obtained using the following formula:

$$R(t) = \frac{(\text{intensity}_{460nm})}{(\text{intensity}_{580nm})}.$$

The data were further reduced by calculating the initial ($R_i$) and final ($R_f$) ratios. These were the average ratio values during part or all of the pre-stimulation period and during sample points during the stimulation period. The fluorescence ratio ($R_f/R_i$) was then calculated and reported as a function of time.

Control responses were obtained by performing assays in the presence of the positive control (Compound 10 or Compound 20), and in the absence of pharmacological agents (DMSO vehicle negative control). Responses to the negative (N) and positive (P) controls were calculated as above. The compound antagonist % activity A was then defined as:

$$A = \frac{X - N}{P - N} \times 100$$

where X is the ratio response of the test compound. Using this analysis method, dose response curves were plotted and $IC_{50}$ and Max % Activity values were generated.

Results:

The IC$_{50}$ and Max % Activity values determined for Compound 7 and Compound 13 are reported in Tables 2 and 3, respectively.

TABLE 2

IC$_{50}$ and Max % Activity of Compound 7 in E-VIPR Assay

| Nav1.8 IC$_{50}$ (uM) | Nav1.8 Max % Activity (%) |
|---|---|
| 0.35 | 98 |

TABLE 3

IC$_{50}$ and Max % Activity of Compound 13 in E-VIPR Assay

| Nav1.8 IC$_{50}$ (uM) | Nav1.8 Max % Activity (%) |
|---|---|
| 1.2 | 99 |

Example 7

Evaluation of Metabolic Stability: In Vitro Microsomal Assay

Materials. Rat, Dog, Monkey and Human liver microsomes (20 mg/mL) were obtained from Xenotech, LLC (Lenexa, Kans.). P-nicotinamide adenine dinucleotide phosphate, reduced form (NADPH), magnesium chloride (MgCl$_2$), and dimethyl sulfoxide (DMSO) were purchased from Sigma-Aldrich.

Methods. 10 mM stock solutions containing the test compound (Compound 10 or Compound 7) were prepared in DMSO. The 10 mM stock solutions were diluted to 100 µM in DMSO. In each cluster polypropylene tube, 190.7 µL of 100 mM phosphate buffer, pH 7.4 was added, then 2.5 µL of liver mocrosomes (20 mg/mL, rat, dog, monkey or human) was added, then a 2 µL aliquot of the 100 µM test compound was added, and the mixture was pre-warmed for 10 minutes. Reactions were initiated by addition of 4.8 µL of pre-warmed NADPH solution (100 mM in 100 mM phosphate buffer). The final reaction volume was 200 µL and contained 0.25 mg/mL rat, dog, monkey or human liver microsomes, 1.0 µM test compound, and 2.4 mM NADPH in 0.1 M potassium phosphate buffer, pH 7.4. The reaction mixtures were incubated at 37° C., and the reactions were quenched at 0, 15, 30 and 60 minutes by adding 200 µL of ice-cold quench solution (ACN:MeOH:0.1% formic acid in water 2:2:1) containing internal standard, n=3 per time point. The tubes were centrifuged and supernatants were analyzed for amounts of the test compound remaining by LC-MS/MS. The HPLC system included a Phenomenex Luna C8 column, 3 micron, 2 mm diameter×30 mm long eluted with a gradient mobile phase consisting of 0.1% formic acid in water or in acetonitrile. The analytes were detected by MS/MS with Electrospray Ionization (ESI) in the mode of multiple reaction monitoring (MRM). The injection volume was 10 µL.

Results. The percentages of Compounds 7 and 10 remaining at each time point during incubation with rat, dog, monkey, and human liver microsomes are reported in FIGS. 1 (rat), 2 (dog), 3 (monkey), and 4 (human) The data is also reported below in Tables 4a (rat), 4b (dog), 4c (monkey) and 4d (human)

TABLE 4a

Rat liver microsome data for Compounds 7 and 10

| Time | Compound 10 (% remaining) | Compound 7 (% remaining) |
|---|---|---|
| 0 min | 100 | 100 |
| 15 min | 108 | 109 |
| 30 min | 102 | 105 |
| 60 min | 87.4 | 92.2 |

TABLE 4b

Dog liver microsome data for Compounds 7 and 10

| Time | Compound 10 (% remaining) | Compound 7 (% remaining) |
|---|---|---|
| 0 min | 100 | 100 |
| 15 min | 85.9 | 86.1 |
| 30 min | 85.4 | 85.8 |
| 60 min | 85.7 | 87.5 |

TABLE 4c

Monkey liver microsome data for Compounds 7 and 10

| Time | Compound 10 (% remaining) | Compound 7 (% remaining) |
|---|---|---|
| 0 min | 100 | 100 |
| 15 min | 96.4 | 97.0 |
| 30 min | 92.4 | 93.3 |
| 60 min | 91.4 | 92.5 |

TABLE 4d

Human liver microsome data for Compounds 7 and 10

| Time | Compound 10 (% remaining) | Compound 7 (% remaining) |
|---|---|---|
| 0 min | 100 | 100 |
| 15 min | 110 | 109 |
| 30 min | 105 | 105 |
| 60 min | 106 | 106 |

Example 8

In Vivo Pharmacokinetic Study

General Procedures. Concentrations of the test compounds in plasma were determined using a high performance liquid chromatography/tandem mass spectrometry (HPLC/MS/MS) method. The test compounds along with the internal standard (IS) were extracted from plasma (20 µL) by direct protein precipitation with acetonitrile (1:25 ratio of plasma/acetonitrile). After centrifugation, the supernatant extract (10 µL) was injected onto the LC/MS/MS system. The HPLC system included a Phenomenex Luna C8 column, 3 micron, 2 mm diameter×30 mm long eluted with a gradient mobile phase consisting of 0.1% formic acid in water or in acetonitrile. The analytes were detected by MS/MS with Electrospray Ionization (ESI) in the mode of multiple reaction monitoring (MRM). The lower limit of quantitation (LLOQ) was 1.00 ng/mL. The linear range of the assay was from 1 to 3000 ng/mL. The assay accuracy was within 20% of the nominal values.

Samples of the cassette dose formulation of the test compounds were assayed with similar HPLC/MS/MS method after dilution first with DMSO and then with blank plasma, with final dilution factor of 1000-fold.

Plasma concentration-time profiles of the test compounds were analyzed by noncompartmental pharmacokinetic methods using PK module in Watson, Version 7.4.2 (Thermo Scientific). Pharmacokinetic parameters including $AUC_{all}$, $AUC_{0-\infty}$, $C_0$, Cl, Vss and $t_{1/2}$ were determined.

Descriptive statistical data of plasma concentrations and pharmacokinetic parameter estimates were calculated, including the mean, standard deviation (SD), and coefficient of variation (% CV) using Microsoft Excel 2010.

Rat IV Study. Compounds 7 and 10 were administered simultaneously in a single intravenous bolus to Male Sprague Dawley rats (n=3) via jugular cannula. The nominal dose of each compound was 0.5 mg/kg. The cassette dosing solution was formulated in D5W with additives Animals had free access to food and water before and after dosing. Blood samples (approximately 0.25 mL each) were collected via a carotid artery catheter prior to dosing and at 0 (predose), 5 min, 10 min, 0.25, 0.5, 1, 2, 4, 8, 12, 24 hours post dose. Each blood sample was collected into a tube that was kept on wet ice and contained potassium EDTA as the anticoagulant. Plasma was separated and stored at approximately −70° C. until analysis.

Figure 5:
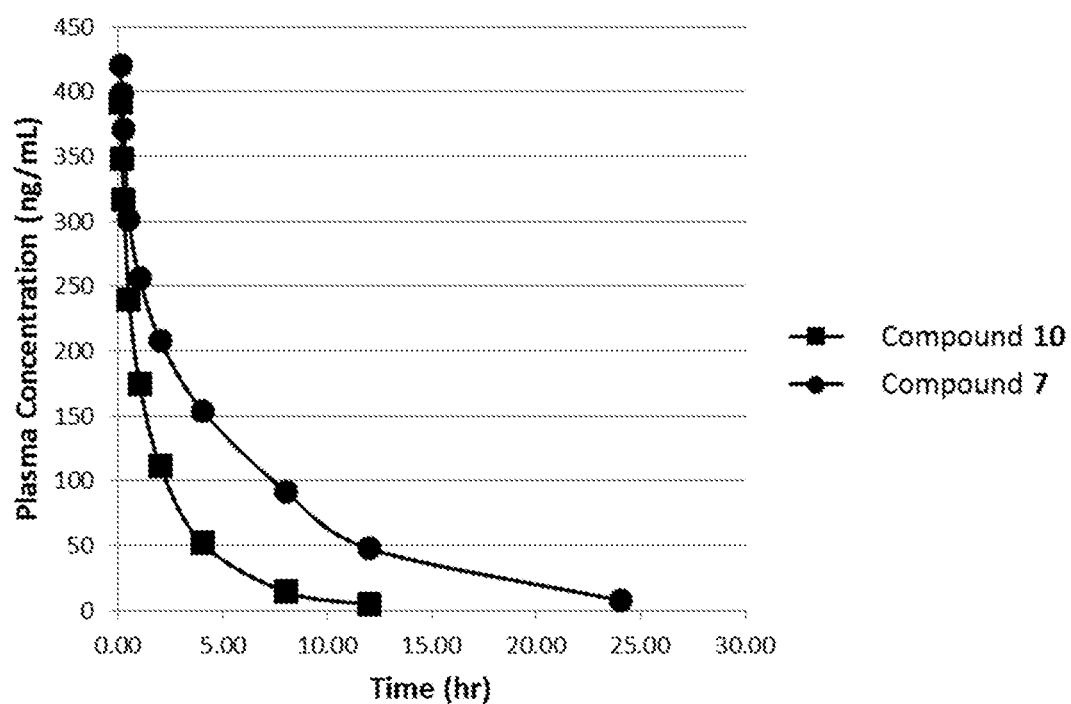
FIG. 5 is a plot of the plasma concentration of Compounds 7 and 10 over time after intravenous administration to Male Sprague Dawley rats.

Plasma samples and dosing solutions were analyzed using a liquid chromatography/tandem mass spectrometry (LC/MS/MS) method to determine the concentrations of Compounds 7 and 10 with a lower limit of quantitation (LLOQ) of 1.00 ng/mL. The average plasma concentrations of Compounds 7 and 10 are plotted in FIG. 5 and are also presented in tabular form in Table 5.

TABLE 5

| Rat IV, plasma concentrations (ng/mL) versus time (hours) | | |
|---|---|---|
| Time (hours) | Compound 10 (ng/mL) | Compound 7 (ng/mL) |
| 0.083 | 391 | 420 |
| 0.167 | 349 | 399 |
| 0.25 | 316 | 371 |
| 0.5 | 239 | 301 |
| 1 | 174 | 256 |
| 2 | 111 | 208 |
| 4 | 51.6 | 154 |
| 8 | 14.3 | 91.3 |
| 12 | 4.27 | 47.6 |
| 24 |  | 7.57 |

Plasma concentration vs. time data were subjected to noncompartmental pharmacokinetic (PK) analysis. The results of this analysis are provided in Table 6. Measured doses of Compounds 7 and 10 are also reported in Table 6. To determined the measured dose of each compound, the dose formulation (50 µL) was aliquoted into a cluster tube at the time of dosing. Then 450 µL of DMSO was added to the tube to dilute it 10×. Then the diluted dosing solution was spiked into rat blank plasma with 100× dilution. The resulting plasma sample was analyzed along with the plasma samples collected from rats that were dosed with the compounds, using the same LC/MS/MS method.

TABLE 6

| Pharmacokinetic Data from Rat IV Study | | | | | | | | |
|---|---|---|---|---|---|---|---|---|
| Dose (mg/kg) | Measured Dose (mg/kg) | Analyte | $C_0$ (ug/ml) | $AUC_{all}$ (ug*hr/ml) | $AUC_{0-\infty}$ (ug*hr/ml) | $t_{1/2}$ (hr) | Cl (ml/min/kg) | Vss (L/kg) |
| 0.5 | 0.560 | 10 | 0.245 | 0.415 | 0.422 | 2.2 | 22.1 | 3.4 |
| 0.5 | 0.464 | 7 | 0.211 | 0.937 | 0.961 | 4.4 | 8.07 | 3.0 |

As shown in Table 6, Compound 7 has a lower clearance and a longer $t_{1/2}$ than Compound 10 in rats.

Many modifications and variations of the embodiments described herein may be made without departing from the scope, as is apparent to those skilled in the art. The specific embodiments described herein are offered by way of example only.

We claim:

1. A compound of formula I:

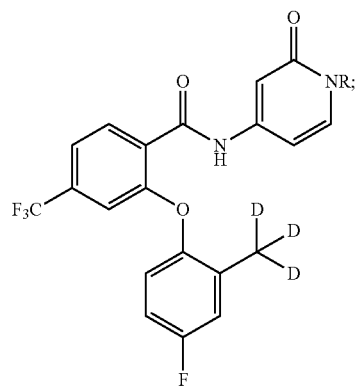 [SMILES: [2H]C([2H])([2H])c1cc(F)ccc1Oc1cc(C(F)(F)F)ccc1C(=O)Nc1cc[nH]c(=O)c1]

or a pharmaceutically acceptable salt thereof, wherein R is H or $CH_2OPO(OH)_2$.

2. The compound of claim 1, or a pharmaceutically acceptable salt thereof, wherein the compound of formula I is

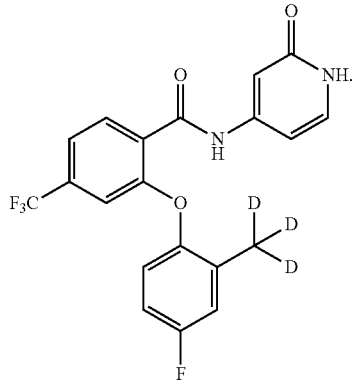 [SMILES: [2H]C([2H])([2H])c1cc(F)ccc1Oc1cc(C(F)(F)F)ccc1C(=O)Nc1cc[nH]c(=O)c1]

3. The compound of claim 1, wherein the compound of formula I is

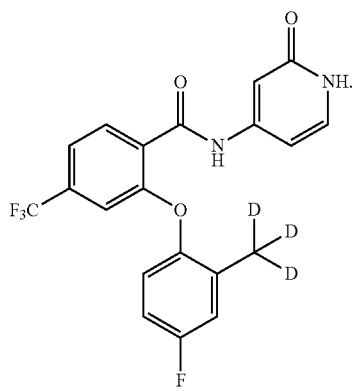

4. The compound of claim 1, or a pharmaceutically acceptable salt thereof, wherein the compound of formula I is

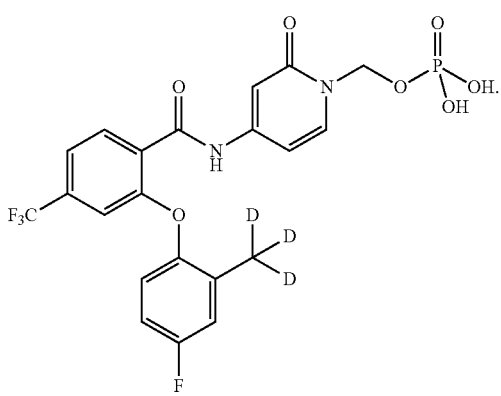 [SMILES: [2H]C([2H])([2H])c1cc(F)ccc1Oc1cc(C(F)(F)F)ccc1C(=O)Nc1ccn(COP(=O)(O)O)c(=O)c1]

5. The compound of claim 1, wherein the compound of formula I is

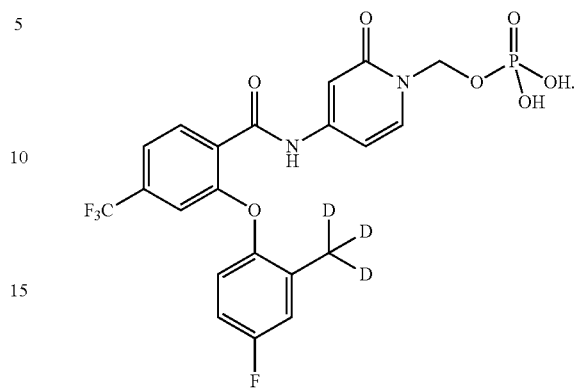

6. A pharmaceutical composition comprising a therapeutically effective amount of the compound or pharmaceutically acceptable salt of claim 1 and one or more pharmaceutically acceptable carriers or vehicles.

7. A pharmaceutical composition comprising the compound or pharmaceutically acceptable salt of claim 1 and one or more pharmaceutically acceptable carriers or vehicles.

8. A method of inhibiting a voltage-gated sodium channel in a subject comprising administering to the subject the compound or pharmaceutically acceptable salt of claim 1.

9. The method of claim 8, wherein the voltage-gated sodium channel is Nav1.8.

10. A method of treating or lessening the severity in a subject of chronic pain, gut pain, neuropathic pain, musculoskeletal pain, acute pain, inflammatory pain, cancer pain, idiopathic pain, postsurgical pain, visceral pain, multiple sclerosis, Charcot-Marie-Tooth syndrome, incontinence, pathological cough, or cardiac arrhythmia comprising administering to the subject an effective amount of the compound or pharmaceutically acceptable salt of claim 1.

11. The method of claim 10, where the method comprises treating or lessening the severity in the subject of neuropathic pain.

12. The method of claim 11, wherein the neuropathic pain comprises post-herpetic neuralgia, idiopathic small-fiber neuropathy, or diabetic neuropathy.

13. The method of claim 10, wherein the method comprises treating or lessening the severity in the subject of musculoskeletal pain.

14. The method of claim 13, wherein the musculoskeletal pain comprises osteoarthritis pain.

15. The method of claim 10, wherein the method comprises treating or lessening the severity in the subject of acute pain.

16. The method of claim 15, wherein the acute pain comprises acute post-operative pain.

17. The method of claim 10, wherein the method comprises treating or lessening the severity in the subject of postsurgical pain.

18. The method of claim 17, wherein the postsurgical pain comprises bunionectomy pain or abdominoplasty pain.

19. The method of claim 10, wherein the method comprises treating or lessening the severity in the subject of visceral pain.

20. The method of claim 10, wherein said subject is treated with one or more additional therapeutic agents administered concurrently with, prior to, or subsequent to treatment with the compound, pharmaceutically acceptable salt, or pharmaceutical composition.

* * * * *